(12) United States Patent
Luyten et al.

(10) Patent No.: US 7,563,596 B2
(45) Date of Patent: *Jul. 21, 2009

(54) METHOD OF MODULATING TISSUE GROWTH USING FRZB PROTEIN

(75) Inventors: Frank P. Luyten, Rockville, MD (US); Malcolm Moos, Jr., Bethesda, MD (US); Bang Hoang, University Heights, OH (US); Shouwen Wang, Rockville, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 293 days.

This patent is subject to a terminal disclaimer.

(21) Appl. No.: 11/184,005

(22) Filed: Jul. 18, 2005

(65) Prior Publication Data

US 2005/0256052 A1 Nov. 17, 2005

Related U.S. Application Data

(63) Continuation of application No. 10/028,051, filed on Dec. 19, 2001, now Pat. No. 6,924,367, which is a continuation of application No. 08/822,333, filed on Mar. 20, 1997, now abandoned, which is a continuation-in-part of application No. 08/729,452, filed on Oct. 11, 1996, now abandoned.

(51) Int. Cl.
*C12P 21/02* (2006.01)
*C12N 5/10* (2006.01)
*C12N 15/12* (2006.01)
*C12N 15/63* (2006.01)

(52) U.S. Cl. ............... 435/69.1; 435/252.3; 435/320.1; 435/325; 435/348

(58) Field of Classification Search .................. None
See application file for complete search history.

(56) References Cited

U.S. PATENT DOCUMENTS 5,418,158 A * 5/1995 Larsen ................... 435/226
5,578,569 A 11/1996 Tam
6,133,232 A 10/2000 De Robertis et al.

FOREIGN PATENT DOCUMENTS

WO WO 96 14335 5/1996
WO WO 97 48275 A 12/1997
WO WO 98/16641 * 4/1998

OTHER PUBLICATIONS

U.S. Provisional Appl. No. 60/020,150, filed Jun. 20, 1996.*
Sambrook et al. Molecular Cloning: A Laboratory Manual. Second Edition, Cold Spring Harbor Laboratory Press, Cold Spring Harbor, New York, U.S.A. Nov. 1989: pp. 16.2 and 17.2.*

Adler, P. N., et al. (1990) Molecular Structure of *frizzled*, a Drosophila Tissue Polarity Gene. *Genetics* 126:401-416.

Aebersold, R. H., et al. (1987) Internal amino acid sequence analysis of proteins separated by one- or two-dimensional gel electrophoresis after in situ protease digestion on nitrocellulose. *Proc. Natl. Acad. Sci. USA* 84:6970-6974.

Bhanot, P., et al. (1996) A new member of the *frizzled* family from *Drosophila* functions as a Wingless receptor. *Nature* 382:225-230.

Bouwmeester T., et al. (1996) Cerberus is a head-inducing secreted factor expressed in the anterior endoderm of Spemann's organizer. *Nature* 382:595-601.

Bowie, J. U., et al. (1990) Deciphering the Message in Protein Sequences: Tolerance to Amino Acid Substitutions. *Science* 247:1306-1310.

Carnac, G., et al. (1996) The homeobox gene *Siamois* is a target of the Wnt dorsalisation pathway and triggers organiser activity in the absence of mesoderm. *Development* 122:3055-3065.

Chan, S. D. H., et al. (1992) Two Homologs of the *Drosophila* Polarity Gene *frizzled* (*fz*) Are Widely Expressed in Mammalian Tissues. *J. Biol. Chem.* 267(35):25202-25207.

Chang, J. T., et al. (1999) Cloning and characterization of a secreted frizzled-related protein that is expressed by the retinal pigment epithelium. *Human Mol. Genetics* 8(4):575-583.

Chang, S.C., et al. (1994) Cartilage-derived Morphogenetic Proteins. *J. Biol. Chem.* 269(45):28227-28234.

Christian, J. L., et al. (1993) Interactions between *Xwnt*-8 and Spemann organizer signaling pathways generate dorsoventral pattern in the embryonic mesoderm of *Xenopus*. *Genes & Development* 7:13-28.

Cui, Y., et al. (1995) *Xwnt*-8b: a maternally expressed *Xenopus Wnt* gene with a potential role in establishing the dorsoventral axis. *Development* 121:2177-2186.

De Robertis, E. M., et al. (1996) A common plan for dorsoventral patterning in Bilateria. *Nature* 380:37-40.

Epifano, O., et al. (1995) Coordinate expression of the three zone pellucida genes during mouse oogenesis. *Development* 121:1947-1956.

Erlebacher, A., et al. (1995) Toward a Molecular Understanding of Skeletal Development. *Cell* 80:371-378.

Finch, P. W., et al. (1997) Purification and molecular cloning of a secreted, Frizzled-related antagonist of Wnt action. *Proc. Natl Acad Sci. USA* 94:6770-6775.

(Continued)

*Primary Examiner*—David S Romeo
(74) *Attorney, Agent, or Firm*—Knobbe Martens Olson & Bear, LLP

(57) ABSTRACT

An isolated cDNA encoding a growth-inducing protein, Frzb, capable of stimulating bone, cartilage, muscle and nerve tissue formation. Frzb binds to and modulates the activity of Wnt growth factors which play a role in various developmental and neoplastic processes. The cDNA and protein sequences of human, bovine and *Xenopus* Frzb are provided. Production and purification of recombinant Frzb are also described.

20 Claims, 7 Drawing Sheets

OTHER PUBLICATIONS

Harland, R. M. (1991) In Situ Hybridization: An Improved Whole-Mount Method for Xenopus Embryos. *Meth. Cell Biol.* 36:685-695.
Hoang, B., et al. (1996) Primary Structure and Tissue Distribution of FRZB, a Novel Protein Related to *Drosophila* Frizzled, Suggest a Role in Skeletal Morphogenesis. *J. Biol. Chem.* 271(42):26131-26137.
Hoppler, S., et al. (1996) Expression of a dominant-negative Wnt blocks induction of MyoD in *Xenopus* embryos. *Genes & Development* 10:2805-2817.
Kao, K. R., et al. (1988) The Entire Mesodermal Mantle Behaves as Spemann's Organizer in Dorsoanterior Enhanced *Xenopus laevis* Embryos. *Develop. Biol.* 36:663-669.
Kay, B. K. (1991) Injection of Oocytes and Embryos. *Methods Cell Biol.* 36:663-669.
Lemaire, P., et al. (1995) Expression Cloning of *Siamois*, a Xenopus Homeobox Gene Expressed in Dorsal-Vegetal Cells of Blastulae and Able to Induce a Complete Secondary Axis. *Cell* 81:85-94.
Leyns, L., et al. (1997) Frzb-1 Is a Secreted Antagonist of Wnt Signaling Expressed in the Spemann Organizer. *Cell* 88:747-756.
Luyten, F. P., et al. (1988) Insulin-like Growth Factors Maintain Steady-State Metabolism of Proteoglycans in Bovine Articular Cartilage Explants. *Archives of Biochem. and Biophys.* 267(2):416-425.
Luyten, F. P., et al. (1989) Purification and Partial Amino Acid Sequence of Osteogenin, a Protein Initiating Bone Differentiation. *J. Biol. Chem.* 264(23):13377-13380.
Luyten, F. P., et al. (1994) Recombinant Bone Morphogenetic Protein-4, Transforming Growth Factor-$\beta_1$, and Activin A Enhance the Cartilage Phenotype of Articular Chondrocytes in Vitro. *Exper. Cell Res.* 210:224-229.
Marieb, E. N. (1992) In, Human Anatomy and Physiology. The Benjamin/Cummings Publ. Co., $2^{nd}$ Ed., 373-375.
Mayr, T., et al. (1997) Fritz: a secreted frizzled-related protein that inhibits Wnt activity. *Mech. Develop.* 63:09-125.
Melkonyan, H. S., et al. (1997) SARPs: a family of secreted apoptosis-realted proteins. *Proc. Natl. Acad. Sci. USA* 94:13636-13641.
Moon, R. T. (1993) In Pursuit of the Functions of the *Wnt* Family of Developmental Regulators: Insights from *Xenopus laevis*, *BioEssays* 15(2):91-97.
Moos, M., Jr., et al. (1995) Anti-Dorsalizing Morphogenetic Protein is a novel TGF-β homolog expressed in the Spemann organizer. *Development* 121:4293-4301.
Moos, M., Jr., et al. (1988) Reproducible High Yield Sequencing of Proteins Electrophoretically Separated and Transferred to an Inert Support. *J. Biol. Chem.* 263(13):6005-6008.
Muthukumaran, N., et al. (1985) Comparison of Bone Inductive Proteins of Rat and Porcine Bone Matrix. *Biochem. Biophys. Res. Comm.* 131(1):37-41.
Nardi, J. B., et al. (1976) Polarity and gradients in lepidopteran wing epidermis. *J. Embryol. exp. Morph.* 36(3):489-512.
Nathan, C. et al. (1991) Cytokines in Context. *J. Cell Biol.* 113(5):981-986.
Nusse, R. et al. (1992) Wnt Genes. *Cell* 69:1073-1087.
Paralkar, V. M., et al. (1989) Affinity of Osteogenin, an Extracellular Bone Matrix Associated Protein Initiating Bone Differentiation, for Concanavalin A. *Biochem. Biophys. Res. Comm.* 160(2):419-424.
Parr, B. A. et al. (1994) *Wnt* genes and vertebrate development. *Cur. Opin. Genet. Develop.* 4:523-528.
Pelton, R. W., et al. (1989) Expression of transforming growth factor β2 RNA during murine embryogenesis. *Development* 106:759-767.
Rattner, A., et al. (1997) A family of secreted proteins contains homology to the cysteine-rich ligang-binding domain of frizzled receptors. *Proc. Nat'l. Acad. Sci. USA* 94:2859-2863.
Richter, K., et al. (1988) Gene expression in the embryonic nervous system of *Xenopus laevis*. *Proc. Natl. Acad. Sci. USA* 85:8086-8090.
Sambrook, J., et al. (Nov. 1989) Molecular Cloning: A Laboratory Manual Second Edition vols. 1, 2 and 3. Cold Spring Harbor Laboratory Press: Cold Spring Harbor, New York USA pp. 16.2, 17.2.
Sato, S. M. et al. (1991) Localized and inducible expression of *Xenopus-posterior* (*Xpo*), a novel gene active in early frog embryos, encoding a protein with a 'CCHC' finger domain. *Development* 112:747-753.
Scales, J. B., et al. (1990) Two Distinct *Xenopus* Genes with Homology to MyoD1 Are Expressed before Somite Formation in Early Embryogenesis. *Mol. Cell. Biol.* 10(4):1516-1524.
Shirozu, M., et al. (1996) Characterization of Novel Secreted and Membrane Proteins Isolated by the Signal Sequence Trap Method. *Genomics* 37:273-280.
Slack, J. M. W. (1994) Inducing factors in *Xenopus* early embryos. *Cur. Biol.* 4(2):116-126.
Smith, W. C. et al. (1991) Injected Xwnt-8 RNA Acts Early in Xenopus Embryos to Promote Formation of a Vegetal Dorsalizing Center. *Cell* 67:753-765.
Smith, W. C., et al. (1995) A *nodal*-Related Gene Defines a Physical and Functional Domain within the Spemann Organizer. *Cell* 82:37-46.
Sokol, S., et al. (1991) Injected Wnt RNA Induces a Complete Body Axis in Xenopus Embryos. *Cell* 67:741-752.
Tempst, P., et al. (1990) Internal sequence analysis of proteins separated on polyacrylamide gels at the submicrogram level: Improved methods, applications and gene cloning strategies. *Electrophoresis* 11:537-553.
Tsukamoto, A. S., et al. (1988) Expression of the *int*-1 Gene in Transgenic Mice Is Associated with Mammary Gland Hyperplasia and Adenocarcinomas in Male and Female Mice. *Cell* 55:619-625.
Van Leeuwen, F. et al. (1995) Oncogene activation and oncogene cooperation in MMTV-induced mouse mammary cancer. *Cancer Biol.* 6:127-133.
Vinson, C. R. et al. (1987) Directional non-cell autonomy and the transmission of polarity information by the *frizzled* gene of *Drosophila*. *Nature* 329:549-551.
Vinson, C. R., et al. (1989) A *Drosophila* tissue polarity locus encodes a protein containing seven potential transmembrane domains. *Nature* 338:263-264.
Vukicevic, S., et al. (1994) Developing Human Lung and Kidney are Major Sites for Synthesis of Bone Morphogenetic Protein-3 (Osteogenin). *J. Histochem. Cytochem.* 42(7):869-875.
Wadsworth, W. G. and Hedgecock, E. M. (1996) Hierarchical guidance cues in the developing nervous system of *C. elegans*. *BioEssays* 18(5):355-362.
Wang, S., et al. (1995) DNA Sequencing from Single Phage Plaques Using Solid-Phase Magnetic Capture. *BioTechniques* 18(1):130-135.
Wang, S., et al. (1997) Frzb, a Secreted Protein Expressed in the Spemann Organizer, Binds and Inhibits Wnt-8. *Cell* 88:757-766.
Wang, Y., et al. (1996) A Large Family of Putative Transmembrane Receptors Homologous to the Product of the *Drosophila* Tissue Polarity Gene *frizzled*. *J. Biol. Chem.* 271(8):4468-4476.
Wolf, V., et al. (1997) DDC-4, an apoptosis-associated gene, is a secreted frizzled relative. FEBS Letters 417:385-389.
Yang-Snyder, J., et al. (1996) A *frizzled* homolog functions in a vertebrate *Wnt* signaling pathway. *Current Biology* 6(10):1302-1306.
Zhao, Z., et al. (1995) A Human Homologue of the *Drosophila* Polarity Gene *frizzled* Has Been Identified and Mapped to 17q21.1. *Genomics* 27:370-373.
Zheng, L., et al. (1995) *frizzled* regulates mirror-symmetric pattern formation in the *Drosophila* eye. *Development* 121:3045-3055.

* cited by examiner

FIG. 1

```
AATAGATGCC GCGGCCCCAG AAGTCTTAGA CGTCGGGAAA GAGCAGCCGG AGAGGCAGGG GGGCGGCCG CTGGCGCTCG GCGCAGCTTT TGGGACCCCA TTGAGGGAAT TtgaTCCAAG
GAAGCTGTGA GATTGCCGGG GGAGGAGAAG CTCCCATATC ATGTGTCCA CTTCCAGGGC GGGGAGGAGG AAACGGGGA CGGGCTTCTC CGCACTGCTG CACCCTGCCC
CATCCTGCCG AGATCATGGT CTGCGGGAGC CGAGGCGGGA TGCTGCTGCT GCCGGCCGGG CTACTCGCCC TGGCTGCGCT CTGCCTGCTC CGCCGCGTGC CGAGCGCGGGC GGCCGGCTGT 35
              M   V   C   G   S   R   G   G   M   L   L   L   P   A   G   L   L   A   A   L   C   L   L   R   V   P   G   A   R   A   *   A   A   C GAGCCCGTTC GCATTCCCCT GTGCAAGTCC CTGCCCCTGA ACATGACTAA ACACCTGACC ACAGCACCCA GGCCAACGCC ATCCTGGCCA TCGAGCAGTT CGAAGGTCTG 75
 E   P   V   R   I   P   L   C   K   S   L   P   W   N   M   T   K   H   L   T   Q   A   P   R   Q   R   I   L   A   I   E   Q   F   E   G   L CTGGGCACCC ACTGCAGCCC GGATCTGCTC TTCTTCCTCT GTGCTATGTA CGCGCCCATC ACTTCCAGCA CGAGCCCTGCA AGCCCCTGCA AGTCTGTGTG CGAGCGGCC 115
 L   G   T   H   C   S   P   D   L   L   F   F   L   C   A   M   Y   A   P   I   C   T   I   D   F   Q   H   E   P   I   K   P   C   K   S   V   C   E   R   A CGGCAGGGT GTGAGCCCAT CCTCATCAAG TACCGCCACT CGTGGCCGGA AAGCCTGGCC TGCGAGGAGC TGCCAGTATA TGACCGCGGC GTGTGCATCT CTCCGGAGGC CATCGTCACT 155
 R   Q   G   C   E   P   I   L   I   K   Y   R   H   S   W   P   E   S   L   A   C   E   E   L   P   V   Y   D   R   G   V   C   I   S   P   E   A   I   V   T GCCGACGGAG CCGATTTTCC TATGGATTCC AGTAATGAA ACTGTAGAGG AGCAAGCAGT GAACGCTGCA AATGTAAACC AGTCAGAGCT ACACAGAAGA CCTATTTCCG AAACATTAC 195
 A   D   G   A   D   F   P   M   D   S   S   N   G   N   C   R   G   A   S   S   E   R   C   K   P   V   R   A   T   Q   K   T   Y   F   R   N   N   Y AACTATGTCA TTCGGGCTAA AGTTAAAGAA ATAAAGACCA AGTGTCATGA CGTTACAGCT GGAGTATCTC GTAGTGGAGG TGAAGGAGAT TTTAAAGGCT TCTCTGGTAA ACATTCCAAG GGAAACTGTG 235
 N   Y   V   I   R   A   K   V   K   E   I   K   T   K   C   H   D   V   T   A   V   V   E   V   K   E   I   L   K   A   S   L   V   N   I   P   R   E   T   V AACCTTTATA CCAGCTCTGG CTGCCTGTGT CCTCCACTTA ACGTTAATGA GGAGTATCTC ATCATGGGCT ACGAAGATGA AGAGCGCTCC AGATTACTGT TGGTAGAAGG TTCTATTGCT 275
 N   L   Y   T   S   S   G   C   L   C   P   P   L   N   V   N   E   E   Y   L   I   M   G   Y   E   D   E   E   R   S   R   L   L   V   E   G   S   I   A GAGAAATGGA AGGATCGACT TGGTAAAAAA GTTAAGCGGT GGGATATGAA CGTCCGTCAT CTTGGACTGA ATACAAGTGA TTCTAGCCAT AGTGATTCCA CTCAGAGTCA GAAGCCTGGC 315
 E   K   W   K   D   R   L   G   K   K   V   K   R   W   D   M   K   L   R   H   L   G   L   N   T   S   D   S   S   H   S   D   S   T   Q   S   Q   K   P   G AGGAATTCTA ACTCCCGGCA AGCACGCACC TAAATCCTGA AATGCAGAAA ATCCTCAGTG GACTTCCTAT TAAGACTTGC ATTGCTGGAC TAGCAAAGGC AAATTGCACT ATTGCACGTC 325
 R   N   S   N   S   R   Q   A   R   N ATAGTCTATT TTTTAGCGAC AAAATCAGG TGGTAACTGA TATTACTTCT ATTTTTTCTT TGTTTTCTG CTTTTCCT TCCCCGATTC CCTTTTTTGT GGTCTGAGTA CAGATCCTTA
AATATATTAT ATGTATTCTA TTTCACTAAT CATGGGAAAA CTGTTCTTTG AAGGGAAAAA CTGTTCATCT GTAAAGCATA AGGGCCTCTT TGCTGGTAGTA AATGTTAATT TGCTGTTCTG
CACCCAGATT GGGAATGCAA TATTGGATGC AAGAGAGAT TTCTGGTATA CAGAGAAAGC TAGATAGGCT GTAAAGCATA CAACAGGCAG CTTTGCTCAT CTAATTACAG CCTCATTCTT GCATGCCTTT
TGGCATTCTC CTCACGCTTA GAAGTTCTA AATGTTTATA AAGGTAAAAT GACAGTTTGA AATCAAATGC AGAAGCACA AGCAATCAAG CACCAGGAAG CATTTATGAA GAAATGACAC
ATGAGATGAA TTATTGCAA GATTGGCAGG AATGCAAAAT AATAGCATTA GGAGCTGGGG ATAGAGCATT TGCCTGACT TGTGACCAGA GAAAGCACA ACTGAAGCTA GTAGCTGGTG GGGTGTTAAC
AGCAGCATT TTCTTTTGAC GATACATTTG TTTGTCTGTG AATATATTGA TCAGCATTAG AGCAGTTGAT CATGCATGGT TATCAGCATA GTCTCTGTTTA ATTTGCTTCC
TTTTAGATGA ACGCATTGT GTCTTTTTT TCTTCTTTTA AAATAATTCT CCCTTGCTGC ATTTGACCAG GAAAAGAAAG CATATATGCA TGTGCACCGG GCTGTTATT TTAAGATATG
TAGCTCTATA AAACGCTATA GTCAAAGAT GCAAGATTCT GGGTGTGTGT ATTAATGTGT ATTATTGTTT GTGTCCGC ATACACTCAC ACTCAAGCTG AACTGAACGA CAGGCCTGTG
CACTGGCCTG CACTTTATCA TTTGGATTTG TGCTGTTTAA TGCTCAGTAA AATATGCTTA ATAAAAGGAA ATAAAAAATA AAAAAAAAA AAAA
```

```
bovine  MVCGSRGGML LLPAGLLALAL ALCLLRVPGA RAAACEPVRI PLCKSLPWNM   50
human   ------P---- --R------- ---------- ---------- ----------   50 bovine  TKMPNHLHHS TQANAILAIE QFEGLLGTHC SPDLLFFLCA MYAPICTIDF  100
human   ---------- ---------- ---------- ---------- ----------  100 bovine  QHEPIKPCKS VCERARQGCE PILIKYRHSW PESLACEELP VYDRGVCISP  150
human   ---------- ---------- ---------- --N------- ----------  150 bovine  EAIVTADGAD FPMDSSNGNC RGASSERCKC KPVRATQKTY FRNNYNYVIR  200
human   ---------- ---------- ---------- --I------- ----------  200 bovine  AKVKEIKTKC HDVTAVVEVK EILKASLVNI PRETVNLYTS SGCLCPPLNV  250
human   ---------- ---------- ----S----- -D-------- ----------  250 bovine  NEEYLIMGYE DEERSRLLLV EGSIAEKWKD RLGKKVKRWD MKLRHLGLNT  300
human   ----I----- ---------- ---------- ---------- --------SK  300 bovine  SDSSHSDSTQ SQKPGRNSNS RQARN                             325
human   ----N----- ---S-----P -----                             325
```

*FIG. 2A*

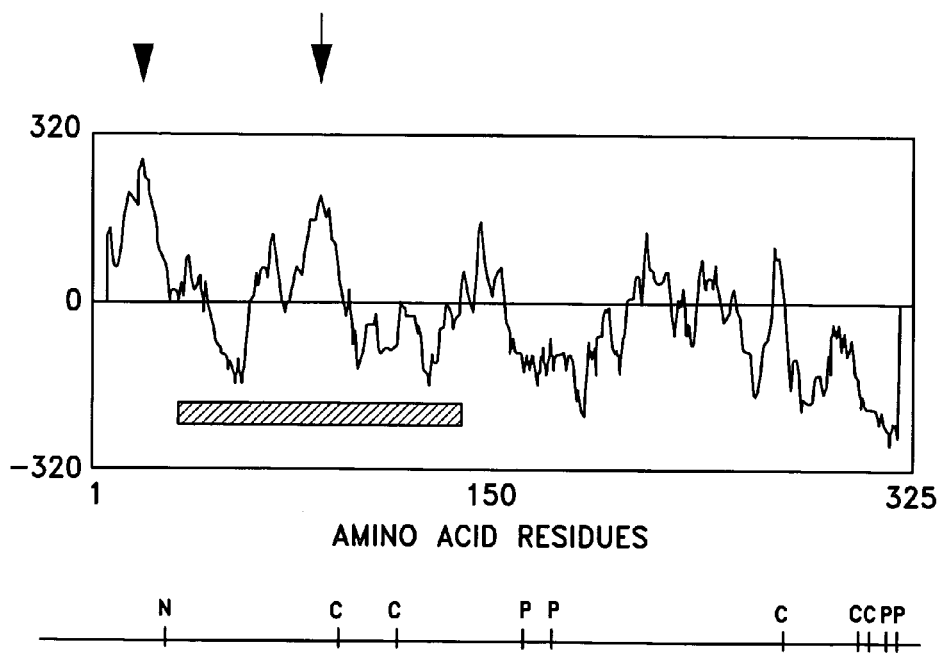

```
Rat fz-1            CQPISIPLCT  DIAYNQTIMP  NLIGHTNQED  AGLEVHQFYP  LVKVQCSAEL  160
Drosophilia frizzled CEPITISICK  NIPYNMTIMP  NLIGHTKQEE  AGLEVHQEAP  LVKIGCSDDL  102
bovine frzb         CEPVRIPLCK  SLPWNMTKMP  NHLHHSTQAN  AILAIEQFEG  LLGTHCSPDL   84
human frzb          CEPVRIPLCK  SLPWNMTKMP  NHLHHSTQAN  AILAIEQFEG  LLGTHCSPDL   84
                    *                                               *

Rat fz-1            KFFLCSMYAP  VCTVLEQALP  --PCRSLCER  A-QCCEALMN  KFGFQWPDTL  207
Drosophilia frizzled QLFLCSLYVP  VCTILERPIP  --PCRSLCES  AR-VCEKLMK  TYNFNWPENL  149
bovine frzb         LFFLCAMYAP  ICTIDFQHEP  IKPCKSVCER  ARQGCEPILI  KYRHSWFESL  134
human frzb          LFFLCQMYAP  ICTIDFQHEP  IKPCKSVCER  ARQGCEPILI  KYRHSWPENL  134
                    *           *           *           *           *

Rat fz-1            KQEKFPVHGR  GELC                                            221
Drosophilia frizzled ECSKFPVHGG  EDLC                                            163
bovine frzb         ACEELPVYDR  G-VC                                            147
human frzb          ACEELPVYDR  G-VC                                            147
                                *
```

METHOD OF MODULATING TISSUE GROWTH USING FRZB PROTEIN

CROSS-REFERENCE TO RELATED APPLICATIONS

This application is a continuation and claims the benefit of priority of U.S. patent application Ser. No. 10/028,051 filed Dec. 19, 2001 now U.S. Pat. No. 6,924,367, which is a continuation and claims the benefit of priority of U.S. patent application Ser. No. 08/822,333 filed Mar. 20, 1997, now abandoned which is a continuation-in-part and claims the benefit of priority of U.S. patent application Ser. No. 08/729,452 filed Oct. 11, 1996, now abandoned all of which are hereby expressly incorporated by reference in their entireties.

FIELD OF THE INVENTION

The present invention relates to a protein isolated from cartilage capable of inducing skeletal morphogenesis, embryonic pattern formation and tissue specification. More particularly, the invention relates to the Frzb protein which induces in vivo cartilage, bone, neural and muscle tissue growth. Frzb also binds to the Wnt family of growth factors and modulates their biological activities

BACKGROUND OF THE INVENTION

The discovery and identification of diffusible factors that regulate skeletal morphogenesis have dramatically improved our understanding of the molecular events governing skeletal pattern formation. Genetic studies have confirmed the importance of these differentiation factors in the formation, growth and maintenance of the skeleton (Erlebacher et al., *Cell*, 80:371-378, 1995). Likewise, non-diffusible molecules, including components of the extracellular matrix and cell surface, are essential to patterning processes. One theory proposed for insect systems is that morphogenesis results from the (re)positioning of cells because of inherent characteristics such as differential adhesiveness (Nardi et al., *J. Embryol. Exp. Morphol.*, 36:489-512, 1976). It is presently unknown whether analogous events occur in mammalian skeletal pattern formation.

In *Drosophila melanogaster*, the cuticle contains hairs and bristles arranged in a defined polarity, of which the pattern and orderly alignment reflect the polarity of the wing epidermis (Adler et al., *Genetics*, 126:401-416, 1990). Typically, these structures are aligned in parallel and point in the same direction as the body surface. Several genetic loci associated with epidermal cell polarity have been studied. One of the most thoroughly investigated is the frizzled (fz) locus. Frizzled encodes an integral membrane protein having seven potential transmembrane domains. The fz locus is required for cellular response to a tissue polarity signal as well as intercellular transmission of that signal along the proximal-distal wing axis (Vinson et al., *Nature*, 329:549-551, 1987; Vinson et al., *Nature*, 338:263-264, 1989). Mutations of the fz locus result in disruption of both cell-autonomous and non-cell-autonomous functions of the fz gene. Strong fz mutations are associated with random orientation of wing hairs, while weaker mutations lead to hair and bristles randomly oriented parallel to neighboring cells with respect to the body axis (Vinson et al., *Nature*, 329:549-551, 1987). Frizzled also regulates mirror-symmetric pattern formation in the *Drosophila* eye (Zheng et al., *Development*, 121:3045-3055, 1995).

The rat and human homologs frizzled-1 and frizzled-2 (fz-1, fz-2) have been cloned and are expressed in a wide variety of tissues including kidney, liver, heart, uterus and ovary (Chan et al., *J. Biol. Chem.*, 267:25202-25297, 1992; Zhao et al., *Genomics*, 27:373-373, 1995). Six novel mammalian frizzled homologs have now been identified (Wang et al., *J. Biol. Chem.*, 271:4468-4476, 1996), each of which appears to be expressed in a distinct set of tissues during development or postnatally.

The basic form and pattern of the skeleton derived from lateral plate mesoderm are first recognizable when mesenchymal cells aggregate into regions of high cell density called condensations which subsequently differentiate into cartilage and bone, and continue to grow by cell proliferation, cell enlargement and matrix deposition. Published PCT Application No. WO 96/14335 discloses the isolation, cloning and in vivo chondrogenic activity of cartilage-derived morphogenetic proteins (CDMPs) which are members of the TGF-β superfamily. Genetic studies have demonstrated that disruption of condensations results in disturbed skeletal phenotypes (Erlebacher et la., *Cell*, 80:371-378, 1995). In humans, limb development takes place over a four week period from the fifth to the eighth week. The upper limbs develop slightly in advance of the lower limbs, although by the end of the period of limb development the two limbs are nearly synchronized. The most proximal parts of the limbs develop somewhat in advance of the more distal parts.

Recently, the number of secreted factors implicated in both limb and axial patterning has increased steadily (Sive, *Genes Dev.*, 7:1-12, 1993; Dawid, *J. Biol. Chem.*, 269:6259-6262, 1994; Hogan, *Genes Dev.*, 10:1580-1594, 1996). Some of these factors are expressed in the Spemann organizer, the region of the *Xenopus* embryo implicated in specification of the dorsal axis and critical to dorso-ventral patterning of the vertebrate embryo. In contrast, the bone morphogenetic protein BMP-4 and Xwnt-8, a member of the Wnt family of growth factors, are expressed in presumptive ventral mesoderm and endoderm early in gastrulation, and are thought to act as positive ventral inducers (Hogan et al., supra; DeRobertis et al., *Nature*, 380:37-40, 1996; Christian et al., *Genes Dev.*, 7:13-28, 1993). Several of these secreted factors are thought to produce their dorsalizing effects by binding to BMP-4 or a related TGF-β class signal and inactivating it. No secreted factor with Wnt binding activity has been identified.

Wnt proteins are implicated in a variety of developmental and neoplastic processes (Nusse et al., *Cell*, 69:1073-1087, 1992; Parr et al., *Curr. Biol.*, 4:523-528, 1994; Moon, *Bioessays*, 15:91-97, 1993). The receptors for these proteins have not been identified. The Wnt family of proteins has been divided into two classes, I and II, based on their ability to induce axis duplication in *Xenopus* oocytes and their transforming activity in mammalian cells. Recently, Frizzled-class proteins were proposed as receptors for the Wnt growth factors (Wang et al., *J. Biol. Chem.*, 271:4468-4476, 1996). This is supported by observations that Wingless protein (Wg), the *Drosophila* prototype of the Wnt family, binds to cells transfected with the frizzled2 gene (Dfz2). Moreover, addition of Wg to cells transfected with Dfz2 causes increased accumulation of Armadillo, a *Drosophila* homologue of β-catenin, an expected consequence of Wg signaling (Bhanot et al., *Nature*, 382:225-230, 1996). In *Xenopus* embryos, overexpression of rat frizzled-1 (Rfz-1) resulted in recruitment of Xwnt-8 and *Xenopus* dishevelled, a component of the Wnt signaling pathway, to the plasma membrane (Yang-Snyder et al., *Current Biol.*, 6:1302-1306, 1996).

There are few known proteins which induce skeletal morphogenesis, as well as induction of nerve and muscle tissue growth. There are no known secreted proteins which will bind to and modulate the function of the Wnt proteins. Such proteins have tremendous therapeutic applications. The present invention provides such a multifaceted protein.

SUMMARY OF THE INVENTION

One embodiment of the present invention is an isolated polynucleotide having the nucleotide sequence shown in SEQ ID NO: 1, 3 or 23.

Another embodiment of the invention is an isolated polynucleotide encoding a native Frzb protein, the polynucleotide capable of hybridizing to a polynucleotide having the nucleotide sequence shown in SEQ ID NO: 1 at 55° C. in 3×SSC, 0.1% SDS.

The present invention also provides an isolated Frzb protein encoded by the polynucleotide described in the preceding paragraph.

Still another embodiment of the invention is an isolated recombinant Frzb protein having the amino acid sequence shown in SEQ ID NO: 2, 4 or 7.

The present invention also provides isolated mammalian Frzb protein having a molecular weight of about 36 kilodaltons.

Another embodiment of the invention is a pharmaceutical composition for inducing cartilage, bone, nerve or muscle growth comprising the isolated Frzb protein encoded by a polynucleotide capable of hybridizing to a polynucleotide having the nucleotide sequence shown in SEQ ID NO: 1 at 55° C. in 3×SSC, 0.1% SDS, or a Frzb protein having the amino acid sequence shown in SEQ ID NO: 2, 4 or 7, in a pharmaceutically acceptable carrier. In one aspect of this preferred embodiment, the carrier comprises fibrin glue, freeze-dried cartilage grafts or collagen. The composition may further comprise cartilage progenitor cells, chondroblasts or chondrocytes. Alternatively, Frzb protein may be coated onto or mixed with a resorbable or nonresorbable matrix. In another aspect of this preferred embodiment, Frzb is mixed with a biodegradable polymer.

A further embodiment of the invention is a method of treating a cartilage, bone, nerve or muscle disorder in a mammal in need thereof, comprising the step of administering to the mammal an effective cartilage, bone, nerve or muscle-inducing amount of any of the pharmaceutical compositions described hereinabove at the site of the disorder. Preferably, the administering step is intravenous, intrathecal, intracranial or intramuscular at the site of the disorder. Advantageously, the mammal is a human.

Another embodiment of the invention is a method of stimulating cartilage formation in a mammal, comprising the steps of combining a protein having the amino acid sequence shown in SEQ ID NO: 2, 4 or 7, or a protein encoded by a polynucleotide capable of hybridizing to a polynucleotide having the nucleotide sequence shown in SEQ ID NO: 1 at 55° C. in 3×SSC, 0.1% SDS, with a matrix to produce a product that facilitates administration of the protein; and implanting the product into the body of a mammal to stimulate cartilage formation at the site of implantation. Preferably, the matrix comprises a cellular material. Advantageously, the mixing step additionally comprises mixing of viable chondroblasts or chondrocytes. In another aspect of this preferred embodiment, the implanting is subcutaneous or intramuscular. Preferably, the mammal is a human.

The present invention also provides a method of modulating Wnt-mediated signaling in a cell, comprising contacting the cell with an effective Wnt-modulating amount of the isolated Frzb protein of claim 3, a Frzb protein having the amino acid sequence shown in SEQ ID NO: 2, 4 or 7 or an active Wnt-modulating fragment thereof. Preferably, the cell is contacted in vivo. Advantageously, the Wnt is Wnt-8, Wnt-1, Wnt-2, Wnt-3, Wnt-4, Wnt-5A, Wnt-5B, Wnt-6, Wnt-7A or Wnt-7B.

Another embodiment of the invention is a method of modulating Wnt-mediated signaling in a cell, comprising contacting the cell with a recombinant construct comprising the coding region of SEQ ID NO: 1, 3 or 23, or encoding an active Wnt-modulating fragment thereof, operably linked to a heterologous promoter in an expression vector. Preferably, the Wnt is Wnt-8, Wnt-1, Wnt-2, Wnt-3, Wnt-4, Wnt-5A, Wnt-5B, Wnt-6, Wnt-7A or Wnt-7B.

Still another embodiment of the invention is a method of inhibiting the growth of a Wnt growth factor-expressing tumor in a mammal, comprising the step of contacting the tumor with an effective tumor growth-inhibiting amount of the isolated Frzb proteins described above. In one aspect of this preferred embodiment, the tumor is a mammary or intestinal tumor. Preferably, the mammal is a human.

The present invention also provides a method of inhibiting the growth of a Wnt growth factor-expressing tumor in a mammal, comprising the step of contacting said tumor with a recombinant construct comprising the coding region of SEQ ID NO: 1, 2 or 23 operably linked to a heterologous promoter in an expression vector. Preferably, the construct is injected into the tumor. Alternatively, the construct is systemically administered to the mammal. Advantageously, the expression vector is a plasmid vector, retroviral vector or adenoviral vector.

Yet another embodiment of the invention are isolated antibodies to Frzb protein having the amino acid sequence shown in SEQ ID NO: 2, 4 or 7.

The present invention also provides a method of facilitating tissue growth or repair, comprising the steps of isolating cells from the tissue; introducing a recombinant construct expressing Frzb into the cells; and returning the cells to the tissue. Preferably, the recombinant construct comprises a retroviral vector, adenoviral vector, herpesvirus vector or adeno-associated viral vector. Advantageously, the tissue is cartilage, muscle, bone or neural tissue.

Another embodiment of the invention is a method of identifying a compound which affects Frzb activity, comprising contacting isolated Frzb with the compound; and determining Frzb activity, wherein an increase in activity compared to Frzb alone indicates that said compound is a Frzb activator and a decrease in activity indicates that said compound is a Frzb inhibitor. In one aspect of this preferred embodiment, the determining step comprises an in vivo chondrogenesis assay.

BRIEF DESCRIPTION OF THE DRAWINGS

FIG. 1 shows the nucleotide (SEQ ID NO: 1) and deduced amino acid sequence (SEQ ID NO: 2) of bovine Frzb. The predicted gene product contains 325 amino acids with a putative signal peptide (boxed). The dashed underline indicates the tryptic peptide sequence used to isolate a cDNA fragment by RT-PCR. Two separate consensus polyadenylation sites are underlined. A "TGA" termination codon is shown in the 5'-untranslated region. The putative signal peptide cleavage site is indicated by the scissors.

FIG. 2A shows a comparison between the deduced amino acid sequences of bovine (SEQ ID NO:2) and human (SEQ ID NO: 4) Frzb. The predicted 23 amino acid signal peptide is boxed. The asterisk indicates a potential N-linked glycosylation site. The putative transmembrane region is underlined and bolded.

FIG. 2B shows a hydropathy plot of human Frzb from the deduced amino acid sequence. The plot was generated by the GeneWorks™ program using the paradigm of Kyte and Doolittle. Hydrophobic residues are in the upper part of the graph. The arrowhead at the amino terminus indicates the potential signal peptide. The putative transmembrane domain is indicated by a downward arrow. N, C, and P are N-glycosylation, casein kinase 2 phosphorylation, and protein kinase C phosphorylation sites, respectively. The stippled bar underneath the plot represents the frizzled-like domain.

FIG. 3 shows an amino acid sequence comparison of the N-terminal domain of bovine (amino acids 35-147 of SEQ ID NO: 2) and human (amino acids 35-147 of SEQ ID NO: 4) Frzb, and their homology with amino acids 111-221 of rat fz-1 (SEQ ID NO: 5) and amino acids 53-163 of *Drosophila* frizzled (SEQ ID NO: 6). Identical residues are denoted by shaded boxes. Gaps indicated by hyphens were introduced to optimize sequence alignment. Asterisks indicate conserved cysteine residues. The numbers to the right indicate amino acid residues for each protein.

DETAILED DESCRIPTION OF THE PREFERRED EMBODIMENTS

The present invention includes polynucleotides encoding Frzb protein isolated from various mammalian tissues, as well as the corresponding protein sequences and variations thereof. Bovine and human Frzb proteins exhibit 94% amino acid identity. An orthologue of Frzb protein, Xfrzb, is also present in *Xenopus laevis* embryos and exhibits about 92% amino acid identity to the corresponding mammalian Frzb proteins in the conserved frizzled-related domain. Bovine articular cartilage extracts were prepared to characterize protein fractions capable of inducing cartilage formation when implanted subcutaneously into rats (in vivo chondrogenic activity). Trypsin digestion of highly purified chondrogenic protein fractions followed by polymerase chain reaction (PCR) using degenerate oligonucleotide primers derived from a 30 residue tryptic peptide of the purified protein led to identification of a cDNA encoding a 36 kDa protein. The amino-terminal domain of the deduced amino acid sequence exhibited about 50% amino acid identity to the corresponding region of the *Drosophila* gene frizzled which is implicated in the specification of hair polarity during development. Because of its homology to frizzled, the protein was named Frzb.

Figure 4:
FIG. 4 shows an amino acid sequence comparison between *Xenopus* Frzb (SEQ ID NO: 7), bovine Frzb (SEQ ID NO: 2) and human Frzb (SEQ ID NO: 4). Amino acids identical among the three sequences are boxed. A consensus sequence (SEQ ID NO:8) is shown. The putative signal peptide cleavage site is shown by the pair of scissors.
Figure 5:
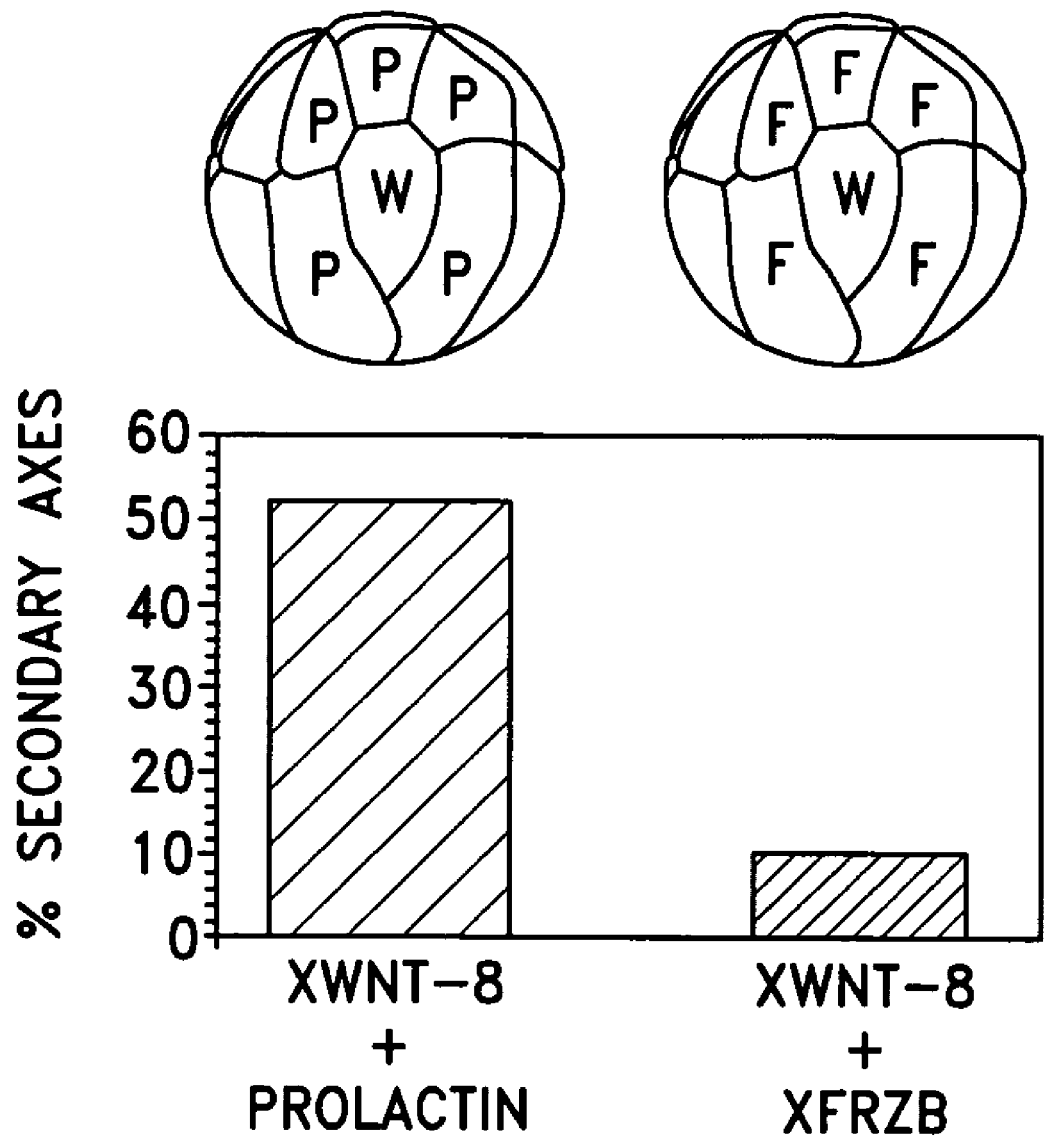
FIG. 5 shows that Frzb can block Wnt-8 signaling across cell boundaries. Ventral *Xenopus* blastomeres were injected with either prolactin (P) or Xfrzb (F) mRNA (50-100 pg per blastomere) as shown at the early 16 cell stage. At the late 16 cell stage, single blastomeres surrounded by those injected previously were injected with Xwnt-8 (W) mRNA (10 pg), and scored for secondary axes. The experiment was performed three times with similar results. Data were pooled for the graph shown in the figure.

The nucleotide and protein sequences of bovine Frzb are set forth in SEQ ID NOS: 1 and 2, respectively. The nucleotide and protein sequences of human Frzb are set forth in SEQ ID NOS: 3 and 4, respectively. The Frzb protein sequences of the invention have the sequences shown in SEQ ID NOS: 2 and 4, or sequence variations thereof which do not substantially compromise the ability of these proteins to induce cartilage, bone, muscle and nerve tissue formation. It will be appreciated that Frzb proteins containing one or more amino acid replacements in various positions of the sequences shown in SEQ ID NOS: 2 and 4 are also within the scope of the invention. Many amino acid substitutions can be made to the native sequence without compromising its functional activity. This assertion is supported by the sequence data shown in FIG. 4. Both the mammalian and *Xenopus* proteins have biological activity. The primary sequence divergence, particularly in the carboxyl terminal region of the molecule that contains the exon-intron boundaries, is wider between the amphibian and mammalian forms of Frzb. These sequence differences do not materially alter the biological activity of the protein.

Variations of these protein sequences contemplated for use in the present invention include minor insertions, deletions and substitutions. For example, conservative amino acid replacements are contemplated. Such replacements are, for example, those that take place within a family of amino acids that are related in the chemical nature of their side chains. The families of amino acids include the basic amino acids (lysine, arginine, histidine); the acidic amino acids (aspartic acid, glutamic acid); the non-polar amino acids (alanine, valine, leucine, isoleucine, proline, phenylalanine, methionine, tryptophan); the uncharged polar amino acids (glycine, asparagine, glutamine, cysteine, serine, threonine, tyrosine) and the aromatic amino acids (phenylalanine, tryptophan and tyrosine). In particular, it is generally accepted that conservative amino acid replacements consisting of an isolated replacement of a leucine with an isoleucine or valine, or an aspartic acid with a glutamic acid, or a threonine with a serine, or a similar conservative replacement of an amino acid with a structurally related amino acid, in an area outside of the polypeptide's active site, will not have a major effect on the properties of the polypeptide.

In fact, any protein derivative of SEQ ID NOS: 2 and 4, including conservative substitutions, non-conservative substitutions, mixtures thereof, as well as truncated peptides or sequence variations thereof may be tested as described in the following examples to determine their ability to induce cartilage, bone muscle and nerve tissue. Such routine experimentation will enable the skilled artisan to screen any desired Frzb protein.

A portion of the isolated bovine frzb cDNA sequence (SEQ ID NO: 1) was used to screen a human placental cDNA library under high stringency conditions (3×SSC, 0.1% SDS, 55° C.; see Example 3), resulting in isolation of a cDNA (SEQ ID NO: 3) encoding a protein having 94% identity to the bovine protein. The *Xenopus* cDNA sequence corresponding to the conserved frizzled-related region exhibits greater than 80% nucleotide sequence identity to both mammalian Frzb genes. Thus, any nucleotide sequence capable of hybridizing to the DNA sequence shown in SEQ ID NO: 1 under these high stringency conditions is within the scope of the invention.

Frzb is recovered in 105,000×g supernatants of lysates prepared from *Xenopus* embryos or Frzb-transfected mammalian cells, indicating that Frzb is a soluble protein. Both mammalian and *Xenopus* Frzb are secreted from *Xenopus* oocytes injected with the respective mRNAs. In addition, secretion of *Xenopus* Frzb in soluble form was shown by incubation of oocytes with $^{35}$S-methionine followed by analysis of culture supernatants by SDS-PAGE. Moreover, mammalian cells transfected with a Frzb expression plasmid secrete Frzb into the culture medium.

Both mammalian and *Xenopus* Frzb were subcloned into the pcDNA3 mammalian expression vector and expressed in *Xenopus* oocytes. This vector contains a CMV promoter which drives expression of the inserted gene. However, other heterologous promoters well known in the art are also contemplated including SV40 and RSV. Bovine and human Frzb were expressed in ATDC5, COS1 and COS 7 cells and partially purified using heparin-Sepharose and Concanavalin A-Sepharose chromatography. The production of Frzb in insect expression systems, particularly baculovirus, is also within the scope of the invention. This protein preparation was used in the functional assays described in the examples presented below. Bovine Frzb was expressed in *E. coli* and purified from inclusion bodies using Ni-NTA affinity chromatography. Many expression vectors suitable for use in eukaryotic expression systems are also within the scope of the present invention, including the LacSwitch™ inducible mammalian expression system (Stratagene, La Jolla, Calif.) and pcDNA3 (Invitrogen, San Diego, Calif.).

In situ hybridization and immunostaining of human embryonic sections demonstrate predominant expression surrounding the chondrifying bone primordia and subsequently in the chondrocytes of the epiphyses in a graded distribution that decreases toward the primary ossification center. Transcripts are present in the craniofacial structures but not in the vertebral bodies. Because it is expressed primarily in the cartilaginous cores of developing long bones during human embryonic and fetal development (6-13 weeks), has in vivo chondrogenic activity and is homologous to *Drosophila* frizzled, Frzb is intimately involved in skeletal morphogenesis via induction of cartilage and bone formation.

As described in the *Xenopus* embryo experiments set forth below (Example 9), both bovine and *Xenopus* Frzb induce formation of secondary body axes which contain neural and muscle tissue, indicating that Frzb is an important protein component in the molecular pathway leading to initial specification of muscle and nerve in vertebrates. Further, both bovine and *Xenopus* Frzb induces molecular markers for muscle (myo D, actin) and nerve (NCAM) tissue. This was determined by explanting ventral marginal zones during gastrulation (stage 10), followed by grafting onto oocytes expressing Frzb and culturing for an appropriate period of time. Explants were removed and assayed for expression of the particular marker; Untreated ventral marginal zones did not express these markers. These results have been obtained with both injection of mRNA into developing vertebrate embryos and with Frzb protein secreted from *Xenopus* oocytes. Thus, overexpression of the gene encoding Frzb will induce the formation of nerve and muscle tissue in vertebrates.

Wnt proteins are a large class of secreted proteins implicated in a wide variety of differentiation and developmental processes (Cui et al., *Development,* 121:2177-2186, 1995; Bhanot et al., *Nature,* 382:225-230, 1996). When myc-tagged XWnt-8 and Frzb were cotransfected in mammalian cells, Frzb was co-immunoprecipitated with an antibody directed against myc (Example 15). When Frzb mRNA was coinjected with X-Wnt8 mRNA into *Xenopus* oocytes, Wnt-mediated induction of dorsal markers was blocked (Example 13). Thus, Frzb binds and inhibits Wnt-8 during *Xenopus* gastrulation, thus preventing inappropriate ventral signaling in developing dorsal tissues. Because Wnts play critical roles in developmental processes and oncogenesis, Frzb is useful as a modulator of tissue formation and as a tumor suppressor agent.

The cysteine-rich frizzled domain is required for binding of Frzb to Wnt-1 and Wnt-5. While several truncated versions of the frizzled domain co-immunoprecipitate with Wnt proteins, the inhibition of Wnt-1-driven axis duplication in *Xenopus* embryos was abolished upon modification of this domain. The C-terminal domain of Frzb appears to support its inhibitory activity, but is not required. The Frzb-Wnt protein interaction was demonstrated for both Wnt-8 and Wnt-1. Co-injection of Frzb and Wnt-5A did not inhibit the formation of the phenotype characteristic of Wnt-5A-injected *Xenopus* embryos. This suggests that the action of Frzb and other related secreted Wnt binding proteins is not always inhibitory, but may also be stimulatory. Thus, Frzb is capable of modulating Wnt activity. The determination of whether Frzb stimulates or inhibit signaling mediated by a particular Wnt protein can be made using an appropriate assay system for the Wnt protein of interest.

To investigate the specificity of Frzb/Wnt interactions, COS7 cells were co-transfected with Frzb and several HA-tagged Wnt family members (Example 17). In contrast to Frzb which was secreted into the medium in these transfected cells, no Wnt protein was detected in the supernatants. Thus, co-immunoprecipitation experiments were performed with COS7 cell lysates and demonstrated a direct protein-protein interaction between Wnt-1, Wnt-8 and Frzb. As described in Example 18, Frzb co-immunoprecipitated with all of the Wnt proteins tested. Likewise, Wnts co-immunoprecipitated with Frzb. These findings demonstrate that Frzb has sufficient affinity for each of these to allow co-immunoprecipitation. Due to this direct interaction with many members of the Wnt protein family, it is likely that Frzb plays a pivotal role in modulating the activity of all these proteins, as well as Wnt proteins from other mammalian cell types.

Lack of soluble Wnt proteins precluded classical binding studies. Frzb-Wnt interactions were investigated using different washing conditions after immunoprecipitation including a variety of salt concentrations and detergents. Increasing salt concentrations in the washing did not affect these interactions. Increasing SDS concentrations resulted in the loss of the interaction, although no differences were observed when Wnt-1 (class I) was compared to Wnt-5A (class II). Taken together, no washing conditions could be identified that suggested any differences in the nature of the interactions between Frzb and Wnt-1 or Wnt-5.

As discussed in Example 19, the frizzled domain of Frzb is required and sufficient for Wnt binding as shown by immunoprecipitation experiments of COS7 cell lysates co-transfected with Wnt-1 and several deletion constructs and Frzb protein was detected in the supernatant in all instances. The removal of the entire extracellular cysteine-rich N-terminal domain (CRD) resulted in loss of co-immunoprecipitation with the Wnts. Several modifications of the frizzled domain could be made without affecting the outcome of the co-immunoprecipitation experiments.

Overexpression of Wnt protein leads to development of mammary tumors in mice (van Leeuwen et al., *Seminars Cancer Biol.,* 6:127-133, 1995; Tsukamoto et al., *Cell,* 55:619-625, 1988). Frzb is particularly useful for systemic or local administration directly into a tumor (e.g. in situ tumors), especially for "wnt-driven" tumors such as mammary and intestinal cancers. Determination of whether a tumor is "wnt-driven" can be made by isolating DNA from the tumor and incubating the DNA with a labeled Wnt probe. Frzb can be combined with a pharmaceutically acceptable excipient and injected directly into a tumor. systemically administered, or the nucleotide sequence encoding bovine, human or *Xenopus* Frzb (SEQ ID NO: 1, 3 and 23, respectively) can be incorporated into an expression vector such as a plasmid, adenoviral vector or retroviral vector by methods well known in the art. These Frzb-containing constructs can be directly injected into a tumor or administered systemically to a mammal.

Frzb or constructs encoding Frzb also can be advantageously enclosed in micelles or liposomes. Liposome encapsulation technology is sell known. Liposomes can be targeted to a specific tissue, such as tumor tissue, through the use of receptors, ligands or antibodies capable of binding the targeted tissue. The preparation of these formulations is well known in the art (see, for example, Radin et al., *Meth. Enzymol.*, 98:613-618, 1983).

Frzb can be used for tissue regeneration, either alone or in conjunction with other morphogenetic proteins, including Wnts, which are implicated in many tissue specification processes. For example, Frzb in conjunction with endogenous Wnt may promote muscle formation and repair. Frzb can also be used to generate tissues or organs ex vivo from autologous, immortalized or xenogeneic cell sources.

Frzb is contemplated for use in the therapeutic induction and maintenance of cartilage, bone, muscle and nerve tissue. For example, local injection of Frzb as a soluble agent is contemplated for the treatment of subglottic stenosis, tracheomalacia, chondromalacia patellae and osteoarthritic disease. Other contemplated utilities include healing of joint surface lesions (i.e. temporomandibular joint lesions or lesions induced post-traumatically or by osteochondritis) using biological delivery systems such as fibrin glue, freeze-dried cartilage grafts and collagens mixed with Frzb and locally applied to fill the lesion. Such mixtures can also be enriched with viable cartilage progenitor cells, chondroblasts or chondrocytes. Repair or reconstruction of cartilaginous tissues using resorbable or non-resorbable matrices (tetracalcium phosphate, hydroxyapatite) or biodegradable polymers (PLG, polylactic acid/polyglycolic acid) coated or mixed with Frzb is also within the scope of the invention. Such compositions may be used in maxillofacial and orthopedic reconstructive surgery. Frzb can also be used as a growth factor for cells of the chondrocyte lineage in vitro. Cells expanded ex vivo can be implanted into an individual at a site where increased chondrogenesis is desired.

The pharmaceutical composition comprising Frzb may also be used to treat or slow neurodegenerative (i.e. Huntington's disease, Alzheimer's disease, spinal cord injuries), myodegenerative (i.e. muscular dystrophy, myasthenia gravis, myotonic myopathies) and osteodegenerative disorders (i.e. osteoporosis, osteitis deformans). A Frzb-containing pharmaceutical composition is administered to an individual in need of facilitated neural, muscle, or bone cell growth in a growth-facilitating amount thereof. The Frzb protein will promote the growth of these tissues. Thus, Frzb is a growth factor or cytokine capable of inducing growth of a variety of tissues. It is also contemplated that Frzb will positively impact the growth of other tissues, including skin and blood vessels. Thus, Frzb-containing compositions may be used for stimulation of wound healing (i.e. lacerations, burns, surgical incisions), promotion of angiogenesis, to prevent rejection in tissue transplantation and as adjuvants to chemotherapy and immunotherapy.

One embodiment of the invention is a pharmaceutical composition comprising the protein shown in SEQ ID NOS: 2 or 4, or sequence variations thereof, in a pharmaceutically acceptable carrier which may be supplied in unit dosage form. Frzb can be administered to an individual in need of facilitated neural, muscle cartilage and bone growth by numerous routes, including intravenous, subcutaneous, intramuscular, intrathecal, intracranial and topical. The compound is combined with a pharmaceutically acceptable carrier prior to administration. Such pharmaceutical carriers are known to one of ordinary skill in the art.

The Frzb compositions for intravenous administration may be in the form of a sterile injectable preparation, such as a sterile injectable aqueous or oleaginous suspension. Frzb may be provided as either a bolus or continuous intravenous, intrathecal or intracranial drip infusion. Because the composition will not cross the blood brain barrier, intrathecal (in the cerebrospinal fluid) or intracranial administration is required for treatment of neurodegenerative disorders. The suspension may be formulated according to methods well known in the art using suitable dispersing or wetting agents and suspending agents. The sterile injectable preparation may also be a sterile injectable solution or suspension in a parenterally acceptable diluent or solvent, such as a solution in 1,3-butanediol. Suitable diluents include, for example, water, Ringer's solution and isotonic sodium chloride solution. In addition, sterile fixed oils may be employed conventionally as a solvent or suspending medium for this purpose, any bland fixed oil may be employed including synthetic mono- or diglycerides. In addition, fatty acids such as oleic acid may likewise be used in the preparation of injectable preparations.

The Frzb composition may be in soluble or microparticular form, or may be incorporated into microspheres or microvesicles, including micelles and liposomes.

Contemplated daily dosages of Frzb for parenteral administration to patients with neurodegenerative, myodegenerative, and osteodegenerative disorders are between about 1 µg and about 100 µg. Particularly preferred daily dosages are between about 10 µg and about 50 µg. This dosage can be administered once per day, or split over 2, 3, 4 or more administrations. Contemplated daily dosages for systemic administration to patients with Wnt-driven tumors or for direct injection into a tumor are between about 100 µg and 1 mg. The exact dosage can be determined by routine dose/response protocols known to one of ordinary skill in the art. In a preferred embodiment, administration of Frzb is continued until no further improvement in the particular disorder is observed.

It is also anticipated that the frzb polynucleotides of the invention will have utility as diagnostic reagents for detecting genetic abnormalities associated with genes encoding Frzb. Such genetic abnormalities include point mutations, deletions or insertions of nucleotides. Diagnostic testing is performed prenatally using material obtained during amniocentesis or chorionic villus sampling. Any of several genetic screening procedures may be adapted for use with probes enabled by the present invention, including restriction fragment length polymorphism (RFLP) analysis, ligase chain reaction or PCR. Mutations in this gene indicate an increased risk of developmental abnormalities.

Drug screening assays can be used to identify activators or inhibitors of the Frzb protein. For example, Frzb is incubated with a particular drug prior to the in vivo chondrogenesis assay described in Example 1 and compared to a control containing Frzb alone. An increase in cartilage growth in the presence of a drug compared to Frzb alone indicates activation of Frzb, while a decrease indicates inhibition of Frzb activity.

The isolation and partial sequencing of a chondrogenic activity present in bovine cartilage is described below.

EXAMPLE 1

Preparation and Activity of Articular Cartilage Extracts

To characterize factors responsible for cartilage inductive activity in articular cartilage, a protein fraction containing potent cartilage inductive activity was isolated as described in PCT Publication No. WO 96/14335, the entire contents of which are hereby incorporated by reference. Articular (metatarsophalangeal joints) cartilage extracts were prepared from newborn calves as described (Chang et al., *J. Biol. Chem.*, 269:28227-28234, 1994, hereby incorporated by reference) to characterize protein fractions with in vivo chondrogenic activity. Briefly, tissues were finely minced and homogenized with a Polytron (top speed, 2×30 seconds) in 20 volumes 1.2 M guanidine hydrochloride, 0.5% CHAPS, 50 mM Tris-HCl, pH 7.2, containing protease inhibitors and extracted overnight at 4° C. as described by Luyten et al. (*J. Biol. Chem.*, 264:13377, 1989), which is hereby incorporated by reference. Extracts were concentrated and exchanged with 6 M urea by diafiltration using an Ultrasette™ (Filtron Technology, Inc., MA) and applied to a 0.5 1 heparin-Sepharose (Pharmacia/LKB, Piscataway, N.J.) column. the column was washed with 5 bed volumes of 6 M urea, 50 mM Tris-HCl, pH 7.4, 0.15 M NaCl, then eluted with 2 volumes 1 M NaCl in the same buffer.

In vivo chondrogenic activity was assayed in a subcutaneous implantation model in rats using a collagenous carrier (Luyten et al., *J. Biol. Chem.*, 264:13377-13380, 1989; Luyten et al., ibid., hereby incorporated by reference). Briefly, a portion of each fraction was assayed by reconstitution with 25 mg guanidine-insoluble collagenous residue of demineralized rat bone matrix according to procedures described by Luyten et al. (ibid.). Implants were recovered after 10 days and alkaline phosphatase activity was measured as a biochemical indicator or cartilage and/or bone formation. Implants were also examined histologically for evidence or cartilage formation using standard procedures known to those of ordinary skill in the art.

The 1 M NaCl eluate of articular cartilage, which contained biological activity, was concentrated by diafiltration and applied to a Sephacryl S-200 HR gel filtration column (XK 50/100, Pharmacia/LKB). After molecular sieve chromatography, bioactive fractions were pooled and exchanged into 50 mM HEPES, pH 7.4, containing 0.15 M NaCl, 10 mM MgSO$_4$, 1 mM CaCl$_2$ and 0.1% (w/v) CHAPS using Macrosep™ concentrators (Filtron). The equilibrated sample was mixed with 1 ml ConA Sepharose (Pharmacia-LKB) previously washed with 20 volumes of the same buffer according to the procedure described by Paralkar et al. (*Biochem. Biophys. Res. Commun.*, 131:37, 1989, hereby incorporated by reference). After overnight incubation on an orbital shaker at 4° C., the slurry was packed into disposable 0.7 cm ID Bio-Rad columns (Bio-Rad, Hercules, Calif.) and washed with 20 volumes of the HEPES buffer to remove unbound proteins. Bound proteins were eluted with 20 volumes of the same buffer containing 0.5 M methyl-D-mannopyranoside. The eluate was concentrated to 200 µl using Macrosep™ concentrators. Macromolecules were precipitated with 9 volumes of absolute ethanol at 4° C. overnight. The precipitate was redissolved in 1 ml 6 M urea, 50 mM Tris-HCl, pH 7.4. Bioactive bound protein was mixed with 2×Laemmli SDS sample buffer (without reducing agents) and analyzed by 12% preparative SDS-PAGE. Gel elution of the separated protein fractions and testing for biological activity was performed as described by Luyten et al. (ibid.). Protein fractions from the 36-40 kDa region were obtained for bioassay by gel elution-following SDS-polyacrylamide gel electrophoresis (SDS-PAGE) and were found to be chondrogenic.

Primary sequencing data from the bioactive fractions were determined by transfer to PVDF membranes for amino terminal sequencing (Moos et al., *J. biol. Chem.*, 263:6005-6008, 1988) or to nitrocellulose membranes for trypsin digestion as previously described (Aebersold et al., *Proc. Natl. Acad. Sci. USA*, 84:6970-6974, 1987; Tempst et al., *Electrophoresis*, 11:537-553, 1990, both of which are hereby incorporated by reference). Tryptic peptides were separated by reverse-phase high performance liquid chromatography (HPLC) (Epifano et al., *Development*, 121:1947-1956, 1995, incorporated by reference), and the sequence of individual peptides was determined using an Applied Biosystems Model 477A sequencer (Applied Biosystems, Foster City, Calif.) with modifications (Tempst et al., ibid.; Tempst et al., *Anal. Biochem.*, 183:290-300, 1989, incorporated by reference).

EXAMPLE 2

Reverse Transcriptase-Polymerase Chain Reaction (RT/PCR)

Two degenerate oligonucleotide primers corresponding to the amino- and carboxyl-terminus of the 30 amino acid tryptic peptide 323 (ETVNLYTSAGCLCPPLNVNEEYLIMGYEFP; SEQ ID NO: 9) were used in RT/PCR to clone cDNAs corresponding to peptide 323:

```
323S:                                    (SEQ ID NO: 10)
5'-GA(A/G)AC(A/C/T)GT(C/G)AA(C/T)CT(C/G/T)TA(C/T)
AC(A/C/G/T)-3';

and

323AS:                                   (SEQ ID NO: 11)
5'-(AG)AA(C/T)TC(A/G)TA(A/C/G/T)CCCAT(A/C/G/T)
AT-3'
```

For RT/PCR, first strand cDNA synthesis was performed with 1 µg poly(A)$^+$ or 5 µg total RNA prepared from bovine articular chondrocytes using random hexanucleotide primers from the cDNA Cycle™ kit (Invitrogen corp., San Diego, Calif.) or 323AS. 323/323AS primer pairs were used in 30 cycles at 94° C. for 1 min, 50° C. for 1 min and 72° C. for 30 sec. PCR products were purified through a Probind™ membrane (Millipore), followed by subcloning with the TA Cloning™ System (Invitrogen). This yielded a 90 base pair (bp) DNA fragment encoding the proper peptide sequence (dashed underline, FIG. 1). The amino acid sequence deduced from the PCR product was the same as the tryptic peptide sequence.

Other tryptic fragments were also sequenced by Edman degradation and had the following sequences: GVCISPEAIVTA(D or H)GADFPM (SEQ ID NO: 12); QGCEPILIK (SEQ ID NO: 13); QGCEPILICAWPPLY (SEQ ID NO: 14) and ETVNLYTSAGCLCPPLNVNEEYLIMGYE (SEQ ID NO: 15). SEQ ID NO: 12 containing the D residue corresponds to amino acids 145-163 of SEQ ID NO: 2. SEQ ID NO: 13 corresponds to amino acids 117-125 of SEQ ID NO: 2. SEQ ID NO: 14 is not found within SEQ ID NO: 2. SEQ ID NO: 15 corresponds to the sequence found within SEQ ID NO: 2 (ETVNLYSSGCLCPPLNVNEEYLIMGYE; SEQ ID NO: 16) except for position 9 at which there is an alanine in SEQ ID NO: 13 and a serine in SEQ ID NO: 16. The proteins containing these amino acid sequences are most likely structurally and functionally related to the isolated cDNA. These peptides are useful in the design of oligonucleotide probes or in the generation of antisera for nucleic acid hybridization and expression cloning, respectively, of other members of the Frzb protein family. This will allow isolation of other Frzb-related proteins from any vertebrate species. cDNA clones were isolated and sequenced as described in the following example.

EXAMPLE 3

Isolation and Sequencing of cDNA Clones

Bovine articular cartilage total RNA was isolated as described (Luyten et al., *Exp. Cell Res.*, 210:224-229, 1994, incorporated by reference). Poly(A)+ RNA was isolated using the PolyATract™ magnetic bead system (Promega, Madison, Wis.). A cDNA library was constructed in a UNIZAP™XR (Stratagene, La Jolla, Calif.) starting from bovine articular cartilage poly(A)+ RNA. The non-degenerate oligonucleotides designed from the 90 base pair fragment amplified by RT/PCR in Example 2 used to screen the articular cartilage cDNA library were:

```
                                           (SEQ ID NO: 17)
323.23:  5'-GCTCTGGCTGCCTGTGTCCTCCACTTAACG-3'

(SEQ ID NO: 18)
323.40:  5'-CCTCCACTTAACGTTAATGAGGAGTATCTC-3'
```

Plaques hybridizing to both oligonucleotides were further purified using standard plaque hybridization procedures (Sambrook et al., *Molecular Cloning: A Laboratory Manual*, 2nd ed., Cold Spring Harbor laboratory Press, Cold Spring Harbor, N.Y., incorporated by reference). A 2.4 kb clone contained a single open reading frame (ORF) with two separate consensus polyadenylation sites and a poly A tail (FIG. 1). A 1.3 kb clone contained a single polyadenylation signal, a short poly A tail and a short 5'-noncoding region. Three other clones lacked the poly A tail but contained longer 5' ends. Because Northern analysis using a bovine cDNA probe revealed corresponding mRNA expression in placenta, a human placental cDNA library was screened to isolate the human orthologue.

Four clones ranging from 1.3 to 1.6 kb were analyzed and all contained the same open reading frame. All clones contained a consensus translation initiation site (Kozak, *J. Biol. Chem.*, 266:19867-19870, 1991) and an in-frame termination codon situated 144 base pairs upstream of the methionine start codon (FIG. 1). The size difference between the bovine and human cDNA inserts (2.4 kb vs. 1.3 kb) is due to a longer 3' untranslated region in the bovine clone (FIG. 1). Based on sequences from these overlapping cDNA clones, the predicted size of both the human and bovine protein is 325 amino acids (FIG. 2A) (36.2 kDa).

The bovine and human amino acid sequences are 94% identical. The deduced protein sequence of both the human and bovine cDNA revealed at least four structural domains (FIGS. 1, 2A, 2B). An amino-terminal hydrophobic stretch of 25 amino acids immediately downstream of the initiation methionine likely represents a signal peptide (von Heijne, *Nucl. Acids Res.*, 14:4683-4690, 1986). A second hydrophobic region of 24 amino acids (residues 75-98), which represents a putative transmembrane domain, is followed be a region containing several potential serine/threonine phosphorylation sites and a serine-rich carboxyl-terminal domain (residues 301-325). Both homologs contain an N-linked glycosylation site at Asn 49, which is amino-terminal of the putative transmembrane domain. A potential C-terminal glycosylation site in the bovine protein was not present in the human homolog.

A search of the Gen Bank™ data base using the BLAST network service at the national Center for Biotechnology Information (NCBI) (Altschul et al, *J. Mol. Biol.*, 215:403-410, 1990) indicated that Frzb has significant identity (about 50%) in the amino-terminal region (from amino acid 35-147) to *Drosophila* frizzled and rat fz proteins (FIG. 3). The homologous region begins shortly after the cleavage site of the predicted signal sequence. The 10 cysteine residues in this region are conserved.

Following isolation of the bovine cDNA, PCR was used to generate a 1 kb fragment containing XhoI sites at both ends. This fragment, representing the bovine open reading frame (bORF), was used to screen a human placenta λgt11 cDNA library (Clontech, Palo Alto, Calif.). Approximately 7×10⁵ plaques from the bovine library and 3×10⁵ plaques from the human library were screened. Hybridizations were performed for 24 hours at 42° C. in 6×SSC, 1×Denhardt's solution, 0.01% yeast tRNA and 0.05% sodium pyrophosphate. The membranes were washed to a final stringency of 3×SSC, 0.1% SDS at 55° C. for 15 minutes (3×SSC=50 mM sodium citrate, pH 7.0, 0.45 M NaCl).

Sequencing was performed using the dideoxy chain termination method (Sanger et al., *Proc. Natl. Acad. Sci. USA*, 74:5463-5467, 1977) and Sequenase™ Version 2.0 DNA polymerase according to the manufacturer's instructions (United States Biochemical Corp., Cleveland, Ohio). The sequencing data were obtained by primer walking and from subclones of restriction fragments into pBluescript SKII (Stratagene). Compressions were resolved by performing the sequencing reactions in the presence of 7-deaza-GTP (U.S. Biochemical).

Bovine Frzb was expressed in *E. coli* and purified therefrom as described below.

EXAMPLE 4

Frzb Protein Expression and Antibody Production

The full-length bovine frzb gene was subcloned into the pcDNA3 mammalian expression vector (Invitrogen, San Diego, Calif.) under control of the CMV promoter and used to transfect ATDC5, COS-1 (ATCC CRL 1650) and COS-7 (ATCC CRL 1651) cells using the LipofectAMINE™ reagent (GIBCO/BRL, Gaithersburg, Md.) according to the manufacturer's instructions. A soluble, secreted Frzb protein was obtained from culture supernatants and partially purified by heparin-Sepharose and Concanavalin A-Sepharose chromatography.

The bovine frzb open reading frame was subcloned in the proper orientation into the XhoI site of pET-28a(+) (Novagen, Madison, Wis.) which contains an amino-terminal stretch of six histidine residues to facilitate purification of the expressed protein as well as a T7 tag for immunodetection. The pET-bORF construct was used in the *E. coli*-based pET System™ to obtain bovine Frzb fusion protein. Purification of protein product from inclusion bodies with Ni-NTA affinity chromatography (QIAGEN) was performed using decreasing pH steps according to the manufacturer's instructions. The affinity purified protein was visualized as a major band following Coomassie blue staining after SDS-PAGE. The identity of the fusion product was verified by immunoblotting using a T7 monoclonal antibody. Rabbits were immunized with Bfrzb fusion protein for 6 months, 250 µg protein per boost, total of 10 injections. Following immunization, several rabbits were subsequently immunized with a synthetic peptide of 12 amino acids (residues 51-61 of FIG. 1) coupled to keyhole limpet hemocyanin (KLH) through a carboxyl-terminal cysteine. The resulting antisera were screened and titered in immunoblots using the Western-Light Plus™ kit (TROPIX, MA) according to the manufacturer's protocol. Briefly, membranes were incubated overnight in blocking buffer (BF) containing 0.6% I-BLOCK™ (TROPIX) in phosphate buffered saline (PBS) and 0.1% Tween-20. The antiserum was diluted from 1:250 to 1:10,000 in BF. The membranes were washed three times for 5 min in BF after each incubation step. The membranes were incubated with secondary antibody at a dilution of 1:20,000 for 30 min, followed by AVDIX™ (enzyme conjugate) incubation for 20 min. Blots were developed using the CSPD™ chemiluminescent substrate (TROPIX) and exposed to Kodak XAR-5 film for 1 to 10 min. Antiserum N374-PEP generated against residues 51-61 of FIG. 1 afforded the optimal signal to noise ratio in Western blots and was thus selected for further studies and immunohistochemical staining. This antibody detected a band migrating at the same apparent molecular weight as the Ni-NTA affinity purified protein as determined by Western blot analysis. This method can be used to generate antiserum to human Frzb, as well as any desired immunogenic fragment of bovine or human Frzb.

Monoclonal antibodies to Frzb can also be generated using conventional hybridoma technology known to one of ordinary skill in the art. Briefly, three mice are immunized with 25 µg recombinant Frzb produced as described in above. Mice are inoculated at 3 week intervals with 20 µg Frzb per mouse (½ subcutaneously and ½ intraperitoneally). Serum collected from each animal after the first inoculation reacts with Frzb as determined by immunoprecipitation. Three days after the final inoculation, mice are sacrificed and the spleens harvested and prepared for cell fusion. Splenocytes are fused with Sp2/0 Ag14 myeloma cells (ATCC CRL 1581) with polyethylene glycol (PEG). Following PEG fusion, cell preparations are distributed in 96-well plates at a density of $10^5$ cells per well and selected in hypoxanthine/aminopterin/thymidine (HAT) medium containing 10% fetal calf serum and 100 U/ml interleukin-6. The medium is replaced with fresh HAT medium 10 days after plating. To identify hybridomas producing MAbs which recognized Frzb epitopes, hybridoma supernatants are tested for the ability to immunoprecipitate purified Frzb or to detect Frzb by immunoblotting.

As previously discussed, Frzb is a secreted soluble protein; however, to determine whether it also exists in a membrane-associated form, the following cell fractionation study was performed.

EXAMPLE 5

Cell Fractionation

A full length 2.4 kilobase (kb) BamHI-XhoI fragment of bovine Frzb (FIG. 1) was cloned into the pcDNA3 expression vector (Invitrogen) to generate the construct pFrzb. COS1 cells ($1.6 \times 10^6$ initial seeding density) were transfected with 10 µg of either pFrzb or the control pcDNA3 vector per 100 mm dish using 120 µl LipofectAMINE™ reagent (GIBCO/BRL, Gaithersburg, Md.). Transfection was carried out for 6 hours in serum-free OPTI-MEM® (GIBCO/BRL). Cells were incubated at 37° C. for 72 hours in serum-free OPTI-MEM® with daily media changes. Conditioned media were then collected and concentrated 20-fold using a Centricon™ 10 microconcentrator (Amicon, Mass.). Cells were scraped from the dishes and resuspended in lysis buffer (10 mM Tris-HCl, 5 mM EDTA, 1 mM phenylmethylsulfonyl fluoride (PMSF)). Cells were lysed using a syringe and a 25-gauge needle and the resulting lysate was collected. The lysate was centrifuged at 3,000×g for 10 min to pellet debris, nuclei and non-lysed cells. The resulting supernatant was centrifuged at 100,000×g for 30 min.

The resulting pellet, containing primarily membrane vesicles, microsomes and other particulates, was extracted successively with: 1) 10 mM Tris-HCl, pH 8.0, 6 M urea; 2) 10 mM Tris-HCl, pH 8.0, 1% Triton X-100, 6M urea; 3) 10 mM Tris-HCl, pH 8.0; and 4) 1% SDS in 1% Triton/6 M urea/10 mM Tris-HCl, pH 8.0. After each extraction, samples were centrifuged at 100,000×g for 30 min. The extracts were then precipitated with an equal volume of 30% trichloroacetic acid (TCA) and re-dissolved in SDS sample buffer. Equal amounts of cytosol, the membrane/particulate fraction and concentrated conditioned media were loaded and separated on 4-20% gradient Tris-glycine gels (Novex, San Diego, Calif.), blotted to Tropifluorm™ PVDF membrane (TROPIX) using a GENIE™ electrophoretic blotter (Idea Scientific, Minneapolis, Minn.) and analyzed by immunoblotting as described in Example 4. The primary antiserum (N374-PEP) dilution was 1:1,000. The urea/SDS/Triton extract of the membrane pellet contained most of the Frzb protein. No protein was detected in the supernatants of the transfected cells or in untransfected cells.

Because the protein sequencing data were obtained from partially purified protein preparations of bovine articular cartilage extracts, similar cell fractionation studies were performed on supernatants and cell extracts of primary bovine articular chondrocyte cultures. Cells were grown to confluence in 100 mm dishes in Dulbecco's Modified Eagle's Medium (DMEM) containing 10% fetal bovine serum (FBS), then incubated for 48 hours in serum free OPTI-MEM® in the presence or absence of dextran sulfate (250 µg/ml) to improve recovery of soluble protein. Conditioned media and cell layers were processed as described above. Again, most of the protein was detected in the membrane associated fractions. The addition of dextran sulfate did not change this distribution.

Thus, Frzb exists in both membrane-associated and soluble forms. Recent evidence suggests that the results of cell fractionation studies depend upon the cell or tissue type and are likely related to cell type specific differences in posttranslational proteolytic processing. Frzb is secreted in soluble form in some, but not all, mammalian expression systems. Importantly, Frzb is soluble in frog embryos as described in Example 14. It is possible that Frzb may occur, and act, in both soluble and particulate forms. Nonetheless, the observation that Frzb can be secreted is highly significant in that soluble protein factors are more amenable to production and formulation. In secreted proteins, the signal peptide is cleaved from the preprotein to form the biologically active secreted molecule. In the mammalian cell expression systems used herein, cell lysates contained two Frzb bands as visualized by Western blots, one corresponding to the unprocessed protein containing the signal peptide, and one corresponding to the processed protein lacking the signal peptide. When Western blots were performed on a clarified lysate of *Xenopus* embryos, a single protein band was observed.

Localization of mRNA encoding Frzb in human embryos was determined by in situ hybridization as described below.

EXAMPLE 6

In Situ Hybridization

Serial sections of human embryos representing various stages of development were used for in vitro hybridization to explore the pattern of Frzb expression during embryonic development. Tissues from human embryos ranging from 6 to 13 weeks of gestation, estimated on the basis of crown-rump length and pregnancy records, were fixed in 4% paraformaldehyde in 0.1 M phosphate buffer (pH 7.2), embedded in paraffin, cut serially at 5-7 µm and mounted on salinated slides. These tissues were obtained from legally sanctioned procedures performed at the University of Zagreb Medical School, Zagreb, Croatia. The procedure for obtaining autopsy materials was approved by the Internal Review Board of the Ethical Committee at the University of Zagreb School of Medicine and the Office of Human Subjects Research of the National Institutes of Health, Bethesda, Md. In situ hybridization was performed as described previously (Pelton et al., *Development*, 106:759-767, 1989; Vukicevic et al., *J. Histochem. Cytochem.*, 42:869-875, 1994). Briefly, after a short prehybridization, sections were incubated overnight at 50° C. in 50% formamide, 10% dextran sulfate, 4×SSC, 10 mM dithiothreitol (DTT), 1×Denhardt's solution, 500 µg/ml freshly denatured salmon sperm DNA and yeast tRNA with 0.2-0.4 ng/ml $^{35}$S-labeled riboprobe ($1 \times 10^9$ cpm/µg) in a humidified chamber. Since the bovine Frzb open reading frame contained XhoI sites at both ends, this fragment was subcloned in both sense and antisense directions into the XhoI site of pBluescript SKII- vector and riboprobes were made using T7 RNA polymerase according to the manufacturer's instructions (Novagen). After hybridization, the sections were washed to a final stringency of 0.1×SSC, 65° C. for 2×15 min. After dehydration in a graded ethanol series containing 0.3 M ammonium acetate, slides were covered with NTB-2 emulsion (Kodak) and exposed for 1-3 weeks. The slides were then stained with 0.1% toluidine blue, dehydrated, cleared with xylene and mounted with Permount.

Between 6 and 13 weeks, no hybridization was detected in most organs, including kidney, heart, muscle, intestine, liver, brain and lung. In contrast, strong hybridization was seen in the developing appendicular skeleton. At six weeks, Frzb transcripts were clearly visible surrounding the early cartilaginous rudiments of the developing limbs, as shown in the distal parts of the upper limb. Hybridization was apparent between neighboring areas of cartilaginous condensation in developing long bones. Subsequently, expression appeared within the cartilaginous cores of developing long bones. This was apparent in the proximal parts of the upper limb, which are more advanced in developmental state than the distal parts. Frzb was also present in the putative limb primordia, thereby bridging the expression data obtained in early development to the localization in developing limbs. Additional experiments in developing limbs have revealed expression in the precartilaginous condensations and subsequently in the future joint interzones.

In addition, Frzb was detected in the cartilage anlagen of several craniofacial bones and the epiphysial ends of the rib cage, while no signal was detected in the vertebral bodies at 6 weeks. At 13 weeks of gestation, Frzb transcripts were present in early chondroblasts of the tarsal bones of the foot, the carpal bones of the hand and the epiphysis of long bones. A striking feature of the expression pattern at this developmental stage was the presence of a graded distribution, most prominent in the phalanges. The highest level of expression was observed at the epiphyses of long bones and at the periphery of cuboidal bones. The expression level then decreased with the appearance of chondrocyte hypertrophy and vascular invasion and appeared to be absent in the primary centers of ossification. Interestingly, at this stage of development, several layers of chondroblasts adjacent to the joint space did not show detectable transcripts. In sharp contrast to the prominent expression observed in other skeletal structures, no expression was apparent in the vertebral bodies at the stages examined.

A *Xenopus laevis* orthologue of Frzb (Xfrzb) was isolated as described below.

EXAMPLE 7

Isolation of XFrzb cDNA

The primers 5'-TGGAACATGACTAAGATGCCC-3' (SEQ ID NO: 19) and 5'-CATATACTGGCAGCTCCTCG-3' (SEQ ID NO: 20) were used to label a region of the bovine Frzb cDNA sequence having a high degree of sequence identity to related genes from human and avian sources. 106 plaques from a Stage 20 *Xenopus* cDNA library prepared in ISH-lox (Novagen, Madison, Wis.) were screened at low stringency (final stringency 35=BOC in 20 mM $Na_2HPO_4$, pH. 7.2, 1 mM EDTA, 1% SDS) and purified plaques were characterized by direct sequencing (Wang et al., *BioTechniques*, 130-135, 1995). One 498 bp clone was 92% identical to a region of the bovine sequence. Two oligonucleotides, 5'-GTCTTTTGGGAAGCCTTCATGG-3' (SEQ ID NO: 21) and 5'-GCATCGTGGCATTTCACTTTCA-3' (SEQ ID NO: 22), corresponding to the 5' and 3' regions of this partial length clone, were used to screen duplicate lifts from a stage 13 library (Richter et al., *Proc. Natl. Acad. Sci. USA*, 8086-8090, 1988). Plaques that hybridized to both oligonucleotides were further analyzed. Several clones containing a complete open reading frame were identified and sequenced. Two closely similar clones were isolated and one of these was chosen for further study. The nucleotide and deduced amino acid sequences of this Xfrzb clone is shown in SEQ ID NOS: 23 and 7, respectively.

Xfrzb shares several features common to the mammalian proteins, including a consensus site for asparagine-linked glycosylation, a conserved cysteine-rich domain characteristic of Frizzled proteins, and a carboxyl terminal motif (amino acids 244-293) that appears homologous to the netrin-specific carboxyl-terminal domain of *C. elegans* unc-6 (Wadsworth et al., Bioassays, 16:3-55-362, 1996).

Expression of Xfrzb was analyzed by in situ hybridization as described in Example 6. Expression begins early in gastrulation and continues as the embryo matures. Thus, it is present when many of the most important events in the establishment of the overall body plan of the developing embryo occur. It is expressed initially in the organizer region, extending beyond it during gastrulation. At the end of gastrulation, expression in this region abruptly ceases and then appears in primordial head mesoderm. Expression then becomes more localized, ultimately to a region corresponding to the developing pituitary gland. These observations are consistent with an important role in the induction of the nervous system and axial musculature, from which the majority of skeletal muscle is derived. Its expression in the pituitary suggests a prominent role in defining anterior mesodermal structures, including the pituitary itself.

EXAMPLE 8

Immunohistochemical Staining

Tissue sections were stained using the Vectastain® elite ABC kit (Vector Laboratories, Burlingame, Calif.) according to the manufacturer's protocol. All embryos were embedded in JB-4 resin (Polysciences, Warrenton, Pa.). For conventional histological analysis, 1-3=B5m sections were cut and stained with hematoxylin and eosin. Before staining, tissue sections were pretreated with chondroitinase ABC for 1 hour. The sections were blocked with PBS and 10% goat serum for 30 min, then incubated for 1 hour with primary antiserum (N374-PEP) at a dilution of 15 µg/ml in PBS containing 0.5% goat serum. In the controls, the primary antibody was replaced with normal pre-immune rabbit serum or secondary antibody alone.

Immunohistochemical staining confirmed the presence of protein in developing skeletal structures, appearing within the cartilaginous cores of the developing long bones. The graded mRNA expression pattern detected by in situ hybridization, most prominent in the phalanges, was paralleled by the protein distribution.

EXAMPLE 9

Ectopic Expression of Frzb in *Xenopus* Embryos

Ectopic expression in developing *Xenopus* embryos induced formation of secondary body axes which contained neural and muscle tissue, but no notochord. This assay is an extremely stringent and specific test for the ability of a gene product to initiate a complex program of developmental events and indicates that Frzb can initiate the synthesis of nerve and muscle tissue. Further, overexpression of Xfrzb in explants fated to develop into ventral tissue induced molecular markers of muscle and nerve tissue.

Ultraviolet irradiation interrupts the normal mechanism for establishment of the dorso-anterior body axis, so that treated embryos did not develop dorsal structures (i.e. head, somites, neural tube, notochord) or the tissues comprising them. When irradiated enzymatically defolliculated embryos were injected with 50 µg mRNA encoding Xfrzb, a body axis was restored. The reconstituted axis contained a neural tube and dysmorphic somites, but no notochord. This experiment is an even more demanding test of the ability of a protein to initiate a complex developmental program. If a truncated construct, containing only the putative extracellular and transmembrane regions of the molecule, was used for injection with mRNA at the two cell stage of one blastomere, one half of the embryo appeared to develop normally, while the other was devoid of both muscle and neural tube; the notochord was normal bilaterally. This study evaluated the effects of ablating the function of Xfrzb, based on the premise that the defective molecule could act as a competitive inhibitor of endogenous Frzb. The effect produced by the defective Frzb was in essence the converse of what is observed if the unmodified gene is overexpressed.

As an initial test of the ability of Frzb to play a role in patterning of the vertebrate embryo, the effects of overexpression and ectopic expression of Frzb in developing *Xenopus* embryos were evaluated.

All embryos were embedded in JB-4 resin (Polysciences, Warrenton, Pa.). for conventional histological analysis, 1-3 µm sections were cut and stained with hematoxylin and eosin; 10-20 µm sections were taken from embryos stained by in situ hybridization. Darkfield images of embryos were photographed with low angle oblique illumination and a Zeiss Stemi-6 dissecting microscope. Embryos cleared with benzyl alcohol/benzyl benzoate and the histological sections in Example 10 was photographed under diascopic illumination with a Nikon FXA microscope. the sections in Example 11 were photographed under multiple oblique illumination (Edge Scientific, Santa Monica, Calif.).

EXAMPLE 10

Dorsalization of Embryos by Frzb

Enzymatically defolliculated single ventral blastomeres at the 4 cell stage were injected with 50 ng bovine Frzb (Bfrzb) mRNA and cultured with oocyte Ringer's solution as previously described (Kay, *Methods Cell Biol.*, 36:657-669, 1991). Frogs and their embryos were maintained and manipulated using standard methods (Gurdon, *Methods Cell Biol.*, 16:125-139, 1977). mRNA injection was performed as described previously (Moos et al., *Development*, 121:4293-4301, 1995). Dorsal and ventral blastomeres were identified by size and pigment variations. Lithium treatment was for 1 hour at 0.1 M (Kao et al., *Dev. Biol.*, 127:64-77, 1988). UV irradiation was performed with a Stratalinker™ (Stratagene). Animal cap explants were cultured in 0.7-1×Marc's Modified Ringer's solution (Kay, supra.). Activin was a gift from the National Cancer Institute and bFGF was from GIBCO/Life Technologies (Gaithersburg, Md.).

Injection of Bfrzb mRNA into single ventral blastomeres produced duplicated posterior dorsal axes reproducibly. Muscle and neural tissues were apparent in frontal sections taken from these embryos, but notochord was absent. The frequency of axis duplication was approximately 15% (24/159; four independent experiments) with Bfrzb and somewhat less with the *Xenopus* gene. The difference may be due to the presence of a consensus translation initiation site (Kozak, *J. Biol. Chem.*, 266:19867-19870, 1991) in the bovine, but not the amphibian sequence. The phenotypes were identical in either case. When Frzb was injected into UV-irradiated embryos. which are incapable of axis formation, dorsal axes were partially rescued in approximately 56% (37/66; three independent experiments). The rescued axes contained muscle and neural tube, but no notochord. Nevertheless, overexpression of Frzb in animal cap explants did not induce markers for mesoderm (Brachyury (Xbra)), neural tube (NCAM), or somites (muscle actin) (not shown).

EXAMPLE 11

Expression of Xfrzb in Developing *Xenopus* Embryo

The Xfrzb open reading frame was subcloned into pCR-Script (Stratagene) to generate probes for in situ hybridization. Both Bfrzb and Xfrzb were subcloned into pSP64R1 (Dr. S. Sokol, Harvard University) for mRNA injection experiments. The pSP64T-Xwnt-8$^{myc}$ plasmid used for mRNA injections and in vitro translation and the CSKA-X8 expression plasmid are described by Christian et al. (*Genes Dev.*, 7:13-28, 1993). A pGEM-5R-Xwnt-8 plasmid (Smith et al., *Cell*, 67:753-765, 1991) was used to generate probes for in situ hybridization. In vitro transcription was performed using mMessage mMachine or MEGAscript kits from Ambion (Austin, Tex.). The plasmid pLNCWnt1HA, containing the open reading frame of mouse Wnt1 and a hemagglutinin (HA) tag near the C-terminus, was provided by Dr. J. Kitajewski (Columbia University). The Xlmf25 plasmid used for in situ hybridization analysis of MyoD is described by Scales et al.

(*Mol. Cell. Biol.,* 1515-1524, 1990). The pfrzb expression plasmid is described by Hoang et al. (*J. Biol. Chem.,* 271: 26131-26137, 1996). In situ hybridization was performed as outlined by Harland (*Methods Cell Biol.,* 36:685-695, 1991), with modifications as described by Moos et al. (*Development,* 121:4293-4301, 1995).

Xfrzb expression first became apparent in the late blastula (stage 9) by in situ hybridization. In early gastrulas (stage 10), mRNA expression was most apparent in the Spemann organizer. In later gastrulas (stage 10.5-11), there was expression in the blastopore lip that extended beyond the organizer as the blastopore lip progressed ventrally. At about stage 11, Xfrzb expression appeared in the dorsal midline. Examination of cleared embryos and corresponding histological sections revealed that this expression was in the involuted mesoderm which is thought to convey signals to the overlying neuroectoderm that participates in specification of the nervous system. Near the onset of neurulation, posterior expression was markedly reduced, and expression in the prechordal plate became apparent. The field of expression was then restricted progressively, stabilizing in the putative pituitary and posteriorly in the vicinity of the proctodeum. Thus, Xfrzb is expressed at the appropriate time and place to participate in specification of the body axis. These results are consistent with RT-PCR analysis.

EXAMPLE 12

Immunoblotting, Immunoprecipitation and in Vitro Translation

Embryos and oocytes were lysed by sonication on ice in 40 mM Tris base, 10 mM EDTA, 1 mM Phenylmethylsulfonyl fluoride (PMSF) in a volume of 10 µl/embryo or oocyte. In some experiments, 20,000×g supernatants were extracted with an equal volume of 1,1,2-trichlorofluoroethane (Evans et al., *Methods Cell Biol.,* 36:117-132, 1991). In vitro translations were performed in the presence of $^{35}$S-methionine with nuclease-treated rabbit reticulocyte lysate and canine pancreatic microsomal membranes (Promega, Madison, Wis.) according to the manufacturer's instructions. β-lactamase mRNA supplied with the kit was used as a positive control for translation and processing and as a negative control for non-specific protein-protein interaction. SDS-PAGE was performed using Novex 10% Nu-PAGE gels (Novex, San Diego, Calif.). Samples from embryos were precipitated with methanol/chloroform (Wessel et al., *Anal. Biochem.,* 138:141-143, 1984) prior to analysis. For metabolic labeling studies, gels were dried onto a single sheet of cellophane and imaged with BioMax MR2 film (Kodak) or a phosphor screen (Molecular Dynamics, Sunnyvale, Calif.).

Immunoprecipitation was performed according to standard procedures (Harlow et al., *Antibodies: a Laboratory Manual,* Cold Spring Harbor Laboratory, Cold Spring Harbor, N.Y., 1988). Antiserum N374-PEP against Xfrzb was prepared as described (Hoang et al., supra.). The clone 9E10 monoclonal antibody (Boehringer, Indianapolis, Ind.) was used for precipitation or detection of the c-myc epitope and hybridoma supernatant containing the 12CA5 monoclonal antibody was used for precipitation of the HA epitope. Immunoblot analyses of separated proteins were performed following transfer to nitrocellulose membranes using 1:20,000 dilutions of primary antisera and 1:100,000 dilutions of peroxidase-conjugated secondary antibody. Bands were detected with the Super Signal Ultra peroxidase substrate (Pierce, Rockford, Ill.).

Endogenous Xfrzb could be detected in early gastrulas (stage 10) and all subsequent stages analyzed by immunoblot analysis. Xfrzb expression was unaffected by bFGF, enhanced by activin or lithium, and suppressed by UV irradiation as described for other genes expressed in the Spemann organizer (Slack, *Curr. Biol.,* 4:116-126, 1994; Kao et al., *Dev. Biol.,* 127:64-77, 1988).

EXAMPLE 13

Blocking of Wnt-8 Signaling In Vivo by Frzb

When Xwnt-8 mRNA is injected during early embryogenesis, secondary dorsal axes with complete head structures are induced reliably (Smith et al., supra.; Sokol et al., *Cell,* 67:741-752, 1991). This phenomenon was used as an in vivo assay for Xwnt-8 activity. When prolactin mRNA was coinjected with Xwnt-8 message, 71% of the embryos (27/38) developed secondary axes. In contrast, when the prolactin mRNA was replaced by an identical amount of Frzb mRNA, axis duplications were suppressed (0/32 for Xfrzb; 1/36 for Bfrzb). Uninjected embryos did not display axial abnormalities.

A Xwnt-8 expression plasmid under the control of the cytoskeletal actin (CSKA) promoter induces the ventrolateral marker Xpo (Sato et al., *Development,* 112:747-753, 1991) and suppresses induction of the dorsal marker goosecoid in activin-treated animal cap explants (Hoppler et al., *Genes Dev.,* 10:2805-2817, 1996). This effect was blocked completely in caps overexpressing a dominant-negative Xwnt-8. Our results confirmed that Xpo expression could be increased by Xwnt plasmid in activin-treated animal cap explants. Importantly, this effect was blocked by XFrzb.

ADMP is a Spemann organizer specific marker that is induced by activin in animal cap explants (Moos et al., supra.). Induction of ADMP by activin was suppressed in explants injected with Xwnt-8 plasmid; this suppression was rescued by Xfrzb. Frzb overexpression did not affect the expression level of Xwnt-8. Thus, Frzb appears to exert its dorsalizing effects by inhibiting the action of Xwnt-8. In a related experiment, the CSKA-Xwnt-8 plasmid was injected into dorsal blastomeres with or without Xfrzb mRNA. In this assay, CSKA-XWnt-8 plasmid produced head defects (64/80 embryos, three independent experiments), as described previously (Christian et al., *Genes Dev.,* 7:13-28, 1993). However, if Xfrzb mRNA was coinjected with the CSKA-Xwnt-8 plasmid, these defects were not observed (0/81 embryos).

Induction of Siamois and Xnr3 proteins (Lemaire et al., *Cell,* 81:85-94, 1995; Smith et al., *Cell,* 82:37-46, 1995) in animal cap explants injected with Xwnt-8 mRNA has been used to assay Xwnt-8 signaling (Carnac et al., *Development,* 122:3055-3065, 1996; Yang-Snyder et al., supra.). Both Xfrzb and Bfrzb blocked the induction of these genes by Xwnt-8.

EXAMPLE 14

Cell Fractionation of *Xenopus* Embryos and Action Across Cell Boundaries

The subcellular distribution of Xfrzb expressed in vivo was analyzed. Endogenous Xfrzb protein was found in 105,000×g supernatants isolated from *Xenopus* embryos, but could not be detected in cell pellets, in contrast to Bfrzb (Example 5). Further, Frzb was secreted by oocytes injected with Frzb mRNA. The apparent molecular weight of 33 kDa is consistent with removal of the putative signal sequence. Proteolytic processing likely accounts for the difference in molecular weight between secreted Frzb and Frzb contained in oocyte lysates.

To determine whether Frzb could act across cell boundaries, an experimental design used to study the dominant-negative Xwnt-8 (Hoppler et al., supra.) was used. Xfrzb reduced the percentage of secondary axes induced by Xwnt-8 from 52% (46/88) to 10% (5/49) when the two mRNAs were injected into different cells. This indicates that the effects of Frzb on Xwnt-8 occur following secretion.

EXAMPLE 15

Direct Interaction of Frzb and X-Wnt8 Proteins

Direct interaction between Frzb and X-Wnt8 proteins was demonstrated in two systems: rabbit reticulocyte lysate containing canine microsomal membranes, and transfected COS cells. COS 7 cells ($1.6 \times 10^6$ initial seeding density) were transfected with 5 μg of pfrzb (see Example 5) or pLNCWnt1HA (see Example 11), or co-transfected with 4 μg pfrzb and pLNCWnt1HA in 100 mm dishes using 30 μl LipofecAMINE™ (Life Technologies, Inc., Gaithersburg, Md.). Transfections were performed for 6 hours in serum-free Opti-MEM I® (Life Technologies). Thereafter, cells were incubated for 18 hours in media containing 10% fetal bovine serum. Subsequently, cells were cultured at 37° C. for 24 hours in serum-free Opti-MEM I®. Cells were extracted for 30 minutes on ice with 50 mM Tris-HCl, 150 mM NaCl, 1.0% NP-40, 0.5% Deoxycholic acid and 0.1% SDS and centrifuged at 12,000×g for 5 minutes. Supernatants were saved for immunoprecipitation.

Xwnt-$8^{myc}$, Bfrzb, Xfrzb, and the β-lactamase control mRNA were all translated and processed in vitro, either alone or in the following combinations: Wnt-8+Frzb, Wnt-8+β-lac; Frzb+β-lac. As expected, the anti-myc antibody precipitated Xwnt-$8^{myc}$ but not β-lactamase, Xfrzb or Bfrzb. Conversely, the 374-PEP antiserum, which recognized both mammalian and amphibian Frzb in immunoblots, precipitated both Xfrzb and Bfrzb, but neither Xwnt-$8^{myc}$ nor β-lactamase. However, when Xwnt-$8^{myc}$ and Frzb were cotranslated, both proteins were precipitated by either the myc-specific 9E10 monoclonal antibody or the 374-PEP antiserum. Identical results were obtained with Bfrzb. Neither reagent precipitated β-lactamase cotranslated with Frzb or Xwnt-$8^{myc}$.

These results were further supported by experiments in which COS7 cells were co-transfected with expression plasmids encoding Bfrzb and an HA-tagged murine Wnt-1, which belongs to the same functional class as Xwnt-8 (Nusse et al., Cell, 69:1073-1087, 1992). Cell lysates were immunoprecipitated with an anti-HA antibody, immunoblotted and probed with the Frzb-specific 374-PEP serum. Frzb protein was detected only in lysates from cells transfected with both Frzb and Wnt-1.

EXAMPLE 16

Frzb Blocks MyoD Expression

Xwnt-8 was implicated in somite development using a carboxy-terminal deletion construct which acted in a dominant negative fashion (Hoppler et al., supra.). Because our data suggested that Frzb could also act as a Wnt inhibitor, we evaluated its effects on somite formation and MyoD expression, both of which are suppressed by the dominant negative Xwnt-8. When Xfrzb mRNA was injected radially into all blastomeres at the four cell stage, trunk development was grossly abnormal, resembling that seen in embryos overexpressing the dominant negative Xwnt-8. Furthermore, Xfrzb blocked MyoD expression both in gastrulating embryos and in activin-treated animal cap explants.

At first glance, the ability of Frzb to induce partial dorsal axes or suppress MyoD expression appear to be incompatible. However, these observations can be reconciled by consideration of the cellular context in which overexpression of Frzb occurs. Ectopic gene expression may generate a secondary axis by a direct inductive effect, or indirectly by inhibition of a ventralizing signal. Frzb blocks the actions of Xwnt-8 as described in Example 13, but does not induce mesoderm, muscle or neural tissue when overexpressed in animal cap explants which do not express Xwnt-8 (Example 10). The dorsalizing actions of Frzb are thus likely to be indirect, resulting from inhibition of the ventralizing effects of Xwnt-8.

Local overexpression of a molecule acting in such an indirect manner produces different effects than generalized overexpression. Injection of Frzb into a single blastomere within the expression domain of Xwnt-8 is expected to block its ventralizing activity locally. Generation of a partial dorsal axis by Frzb (Example 10) is consistent with this prediction. On the other hand, generalized overexpression will block all actions of Xwnt-8 throughout the embryo, including both its ventralizing activity and its effects on somite formation.

Recently, a dominant-negative Xwnt-8 was shown to suppress development of the trunk and somites (Hoppler et al., Genes Dev., 10:2805-2817, 1996). When Frzb was overexpressed using an identical protocol (all blastomeres at the four cell stage), the same phenomenon was produced (Example 16). Thus, the induction of muscle tissue by local overexpression of Frzb in one type of experiment and suppression of somite development by generalized overexpression in another are compatible findings consistent with the conclusion that Frzb acts through inhibition of Xwnt-8 signaling.

To investigate the specificity of Frzb/Wnt interactions, COS7 cells were co-transfected with Frzb and several HA-tagged Wnt family members as described below.

EXAMPLE 17

Transient Transfection of COS7 Cells

Figure 6:
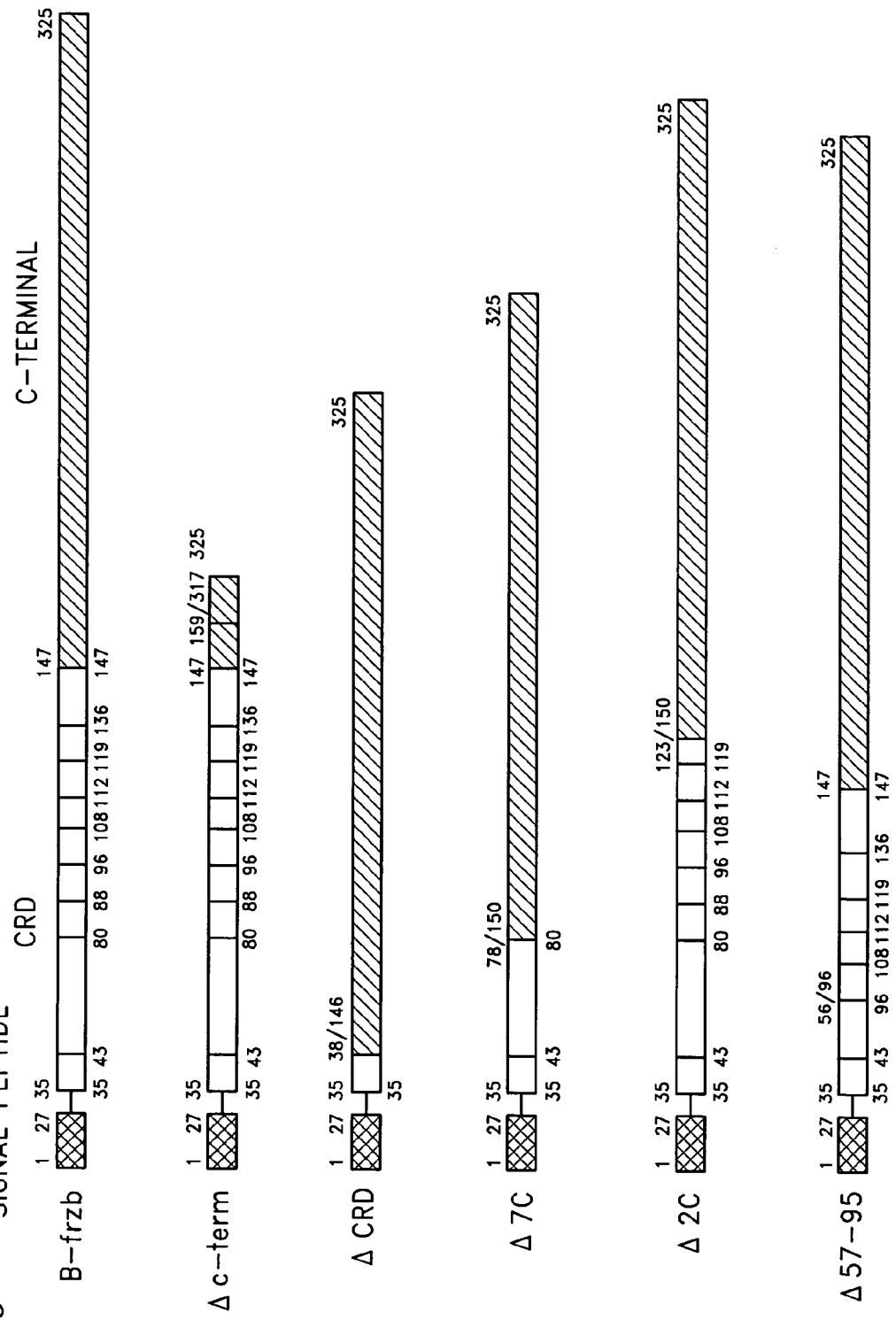
FIG. 6 is a schematic diagram of the BFrzb and Frzb deletion constructs used for transfection of COS7 cells.

Plasmids used for transfection of COS7 cells were as follows. Δc-term was made by deletion of most of the C-terminal region of Frzb from amino acids 160 to 316. ΔCRD was made by deletion of most of the frizzled domain of Frzb from amino acids 39 to 145 including nine conserved cysteines (C43-147). Δ7C was made by deletion in the frizzled domain of amino acid 79 to 149 including seven conserved cysteines (C88-147). Δ2C was made by a deletion in the frizzled domain from amino acid 124 to 149, including two conserved cysteines (C136-147). Δ57-95 was made by deletion in the frizzled domain from amino acids 57 to 95 which interrupted the hydrophobic structure in the frizzled domain. These constructs are shown in FIG. 6. pFrzb-FLAG was made by replacement of the last seven residues of Frzb by a FLAG-tag. All constructs were subcloned into pcDNA3 (Invitrogen). The following plasmids carried ten mouse Wnt gene family members: pLNCW1-HA, pLNCW2-HA, pLNCW3A-HA, pLNCW3B-HA, pLNCW4-HA, pLNCW5A-HA, pLNCW5B-HA, pLNCW6-HA, pLNCW7A-HA and pLNCW7B-HA.

COS7 cells ($1.6 \times 10^6$ initial seeding density) were transfected either with 5 μg plasmid DNA, or co-transfected with 4 μg for each plasmid per 100 mm dish using 30 μl LipofectAMINE™ reagent (GIBCO/BRL). Transfections were carried our for 6 hours in serum-free Opti-MEM I® (GIBCO/BRL). Equal amounts of 10% FBS in Opti-MEM I® were added to the transfections and the cultures were continued for 18 hours. the cells were then incubated at 37° C. for 24 hours in serum-free Opti-MEM I®. The cells were extracted for 30 minutes on ice with 50 mM Tris-HCl, 150 mM NaCl, 1.0% NP-40, 0.5% deoxycholic acid and 0.1% SDS.

EXAMPLE 18

Immunoprecipitations with HA and FLAG Antiserum

Fifty µl of protein A-agarose (Behringer Mannheim GmbH, Germany) was incubated with 100 µl hybridoma supernatant of anti-HA antibody 12CA5 in 450 µl of 50 mM Tris-HCl, pH 7.4, 150 mM NaCl by rotating overnight. 100-400 µl of the cell lysates from transfected COS7 cells and 0-300 µl of RIPA buffer were added to the mixture to a final volume of 1 ml and incubation was continued for another hour. The agarose beads were washed by centrifugation at 12,000×g for 20 seconds, followed by rotation for 20 minutes twice in 1 ml of 50 mM Tris-HCl, pH 7.4, 150 mM NaCl, pH 7.5; twice in 1 ml 50 mM Tris-HCl, pH 7.4, 500 mM NaCl and once in 50 mM Tris-HCl, pH 7.4, respectively, and centrifuged at 12,000×g. After the last wash and centrifugation, pellets were suspended in 30-50 µl of 2×Laemmli sample buffer with 4% β-mercaptoethanol, boiled, separated on 4-20% gradient Tris/Glycine gels (Novex), blotted onto Immobilon™-P membranes (Millipore) and analyzed by immunoblotting.

Membranes were blocked for 30 min in blocking buffer (BF) consisting of 1 M Tris-HCl, pH 7.5, 0.9% NaCl, 0.05% Tween-20 and 4% BSA. The primary antiserum (N374-PEP) was incubated with the membranes in 1/10 BF and 9/10 TBST buffer (10 mM Tris-HCl, pH 7.5, 0.1% Tween, 150 mM NaCl) at a dilution of 1:2,500. The membranes were washed four times for 5 min in TBST after each incubation step. The membranes were then incubated with the secondary antibody at a dilution of 1:10,000 for 60 minutes. Blots were developed using the SuperSignal™ CL substrate system (Pierce) for chemiluminescent detection and exposed to Kodak XAR-5 film for 1 to 10 minutes.

Fifty µl protein G-agarose (Behringer Mannheim) and 5 µg Anti-FLAG M2 antibody (Eastman Kodak) were used for immunoprecipitation; a 1:1,000 dilution of Anti-HA-peroxidase antibody (HRP-HA) (Behringer Mannheim) was used for immunoblotting and SuperSignal™ ULTRA substrate (Pierce) was used for the chemiluminescent detection.

Frzb co-immunoprecipitated with all the Wnts tested (Wnt-1, Wnt-2, Wnt-3A, Wnt-3B, Wnt-4, Wnt-5A, Wnt-5B, Wnt-6, Wnt-7A and Wnt-7B). Likewise, using a flag-tagged BFrzb cDNA, Wnts co-immunoprecipitated with Frzb. Thus, Frzb has sufficient affinity for each of these Wnt proteins to allow co-immunoprecipitation.

EXAMPLE 19

Modulation of Wnt Activity by Frzb In Vivo

Figure 7:
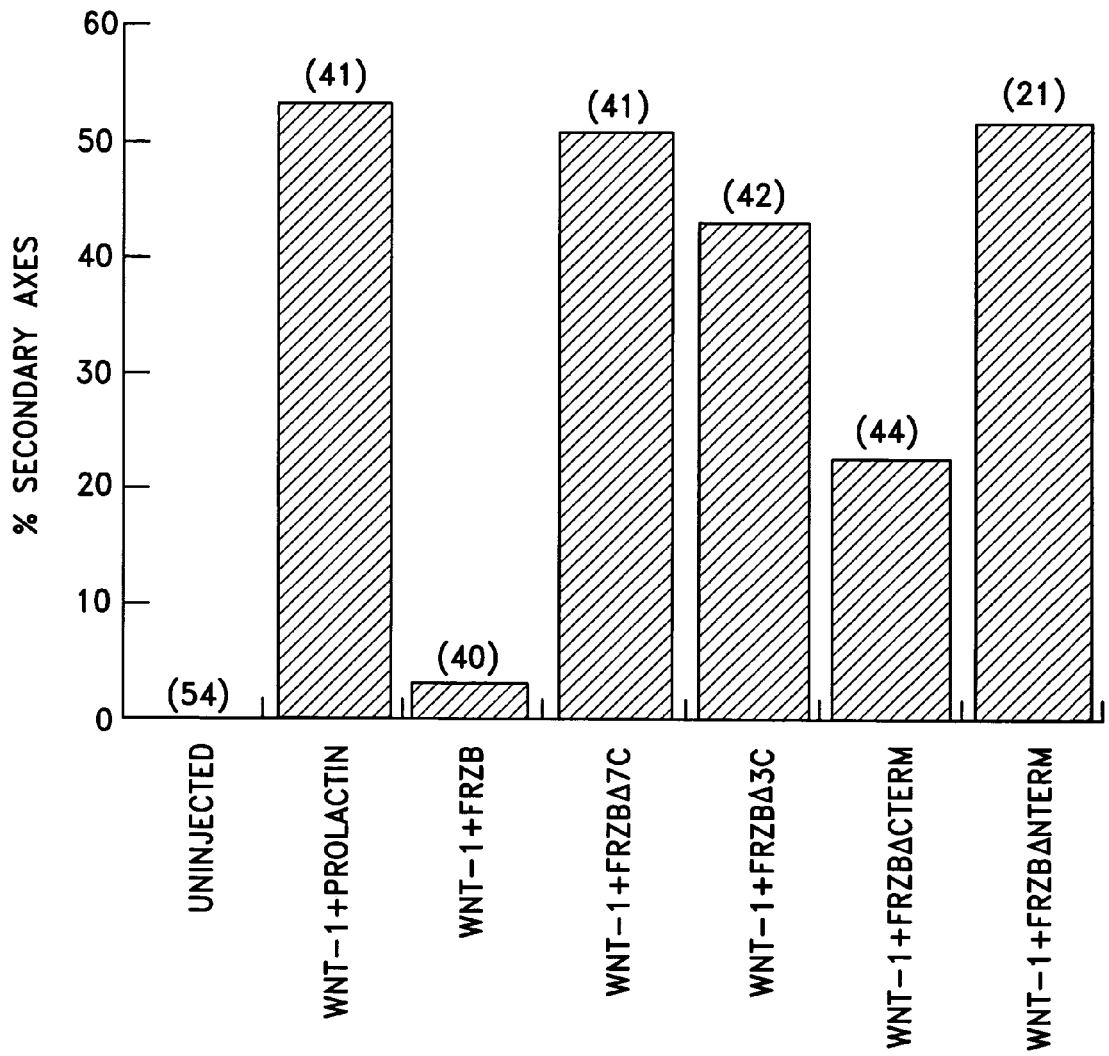
FIG. 7 is a graph illustrating the inhibition of Wnt-1-mediated secondary axis formation by Frzb and the effect of various Frzb deletions on its ability to inhibit Wnt-1-mediated signaling. The constructs are shown in FIG. 6.

Injection of Wnt-1 mRNA into *Xenopus* embryos results in duplication of the dorsal axis and can easily be scored by direct inspection. Co-injection of Wnt-1 and Frzb resulted in the complete inhibition of secondary axis formation due to blockade of Wnt signaling (FIG. 7). Removal of the entire frizzled domain abolished the inhibitory activity of Frzb. Substantial inhibition of Wnt-1-mediated axis duplication was also observed when the CRD only was co-injected with Wnt-1. The C-terminal domain plays a role in this effect, as inhibition was more efficient in the presence of this domain. This suggests a possible role of the C-terminal domain in the stabilization of its tertiary structure affecting the binding affinity to Wnts, a possible involvement in Frzb turnover and increased solubility of the protein. In contrast to the co-immunoprecipitation data, no inhibition was observed in this in vivo assay with any of the deletion constructs affecting the CRD domain.

Wnt-5A was also co-injected with Frzb in *Xenopus* oocytes. Surprisingly, although Frzb binds Wnt-5A, no inhibition of Wnt-5A activity was observed. Co-injection of Wnt-5A and Frzb actually resulted in more pronounced changes in embryo phenotype. Thus, Frzb and related proteins are not always inhibitory and can be considered modulators or Wnt activity. Frzb may restrict Wnt activities and strictly regulate boundaries in certain systems by immobilizing Wnts in the cell, to the cell membrane or the pericellular matrix, while in other systems Frzb may function as a soluble factor enhancing Wnt secretion and even providing transportation to neighboring cells.

EXAMPLE 20

Treatment of Deep Knee Defects with Frzb

A young patient having a large defect in the articular surface of the knee joint is identified. A periosteal flap is obtained from the bone beneath the joint surface of rib cartilage according to standard surgical procedures. The tissue flap is pre-incubated in a solution containing recombinant human, bovine or *Xenopus* Frzb protein. The Frzb-treated periosteal flap is then attached over the lesion in the articular surface of the knee joint by a sewing procedure using, for example, resolvable material. The joint is then closed and injected with a solution containing bovine, human or *Xenopus* Frzb protein in a pharmaceutically acceptable carrier. Injections are administered until cartilage repair is complete. The patient notices markedly less joint pain as the cartilage repair process progresses. Examination by arthroscopy indicates repair of the lesion within several weeks following the initial procedure.

It is also contemplated that gene therapy protocols based on expression of Frzb cDNAs or genomic constructs can be used to facilitate in vivo cartilage, bone, muscle and nerve repair. Therapy may be achieved by genetically altering synoviocytes, periosteal cells, chondrocytes, myoblasts, osteoblasts or neural cells by transfection or infection with recombinant constructs directing expression of Frzb. Such altered cells can then be returned to the appropriate in vivo location. Gene transfer can be performed using numerous vectors well known in the art, including retroviruses, adenoviruses, herpesviruses and adeno-associated viruses.

Both in vivo and ex vivo approaches are anticipated for continuous delivery of Frzb for treating neuro-, myo-, osteo- and chondrodegenerative disorders. In addition, inducible promoter constructs may be employed in gene therapy applications of the present invention.

It should be noted that the present invention is not limited to only those embodiments described in the Detailed Description. Any embodiment which retains the spirit of the present invention should be considered to be within its scope. However, the invention is only limited by the scope of the following claims.

What is claimed is:

1. A vector which contains a nucleotide sequence encoding frzb protein wherein said nucleotide sequence has a sequence selected from the group consisting of SEQ ID NO: 1, SEQ ID NO: 3, SEQ ID NO: 23, and a nucleotide sequence that encodes SEQ ID NO: 2, SEQ ID NO: 4, or SEQ ID NO: 7.

2. An expression vector which contains a nucleotide sequence encoding frzb protein operably linked to a promoter and wherein said nucleotide sequence has a sequence selected from the group consisting of SEQ ID NO: 1, SEQ ID NO: 3, SEQ ID NO: 23, and a nucleotide sequence that encodes SEQ ID NO: 2, SEQ ID NO: 4, or SEQ ID NO: 7.

3. A cell or culture of cells containing the expression vector of claim 2.

4. The cell or culture of cells of claim 3, wherein said cell or cells is/are of mammalian origin.

5. The cell or culture of cells of claim 3, wherein said cell or cells is/are of bacterial origin.

6. The cell or culture of cells of claim 3 wherein said cell or cells is/are of insect origin.

7. The vector of claim 1 wherein the sequence is SEQ ID NO: 1 or a nucleotide sequence that encodes SEQ ID NO: 2.

8. The vector of claim 1 wherein the sequence is SEQ ID NO: 3 or a nucleotide sequence that encodes SEQ ID NO: 4.

9. The vector of claim 1 wherein the sequence is SEQ ID NO: 23 or a nucleotide sequence that encodes SEQ ID NO: 7.

10. A method for producing a polypeptide comprising culturing the cell or culture of cells of claim 3 under conditions in which the nucleotide sequence is expressed.

11. An isolated nucleic acid molecule having the nucleotide sequence of SEQ ID NO: 1, SEQ ID NO: 3, SEQ ID NO: 23, or a nucleotide sequence that encodes SEQ ID NO: 2, SEQ ID NO: 4, or SEQ ID NO: 7.

12. The isolated nucleic acid molecule of claim 11 having the nucleotide sequence of SEQ ID NO: 1 or a nucleotide sequence that encodes SEQ ID NO: 2.

13. The isolated nucleic acid molecule of claim 11 having the nucleotide sequence of SEQ ID NO: 3 or a nucleotide sequence that encodes SEQ ID NO: 4.

14. The isolated nucleic acid molecule of claim 11 having the nucleotide sequence of a SEQ ID NO: 23, or a nucleotide sequence that encodes SEQ ID NO: 7.

15. The isolated nucleic acid molecule of claim 12 having the nucleotide sequence of SEQ ID NO: 1.

16. The isolated nucleic acid molecule of claim 13 having the nucleotide sequence of SEQ ID NO: 3.

17. The isolated nucleic acid molecule of claim 14 having the nucleotide sequence of a SEQ ID NO: 23.

18. The vector of claim 1, wherein the sequence is SEQ ID NO: 1.

19. The vector of claim 1, wherein the sequence is SEQ ID NO: 3.

20. The vector of claim 1, wherein the sequence is SEQ ID NO: 23.

* * * * *

SEQUENCE LISTING

<160> NUMBER OF SEQ ID NOS: 23

<210> SEQ ID NO 1
<211> LENGTH: 2374
<212> TYPE: DNA
<213> ORGANISM: Bos taurus

<400> SEQUENCE: 1

| | | | | | |
|---|---|---|---|---|---|
| aatagatgcc | gcggcccag | aagtcttaga | cgtcgggaaa | gagcagccgg | agaggcaggg | 60 |
| gcggcggcgg | ctggcgctcg | gcgcagcttt | tgggacccca | ttgagggaat | ttgatccaag | 120 |
| gaagctgtga | gattgccggg | ggaggagaag | ctcccatatc | attgtgtcca | cttccagggc | 180 |
| ggggaggagg | aaacggcgga | gcgggcctct | cggcgttctc | cgcactgctg | caccctgccc | 240 |
| catcctgccg | agatcatggt | ctgcgggagc | cgaggcggga | tgctgctgct | gccggccggg | 300 |
| ctactcgccc | tggctgcgct | ctgcctgctc | cgcgtgcccg | gagcgcgggc | ggccgcctgt | 360 |
| gagcccgttc | gcattcccct | gtgcaagtcc | ctgccctgga | acatgactaa | gatgcccaac | 420 |
| cacctgcacc | acagcaccca | ggccaacgcc | atcctggcca | tcgagcagtt | cgaaggtctg | 480 |
| ctgggcaccc | actgcagccc | ggatctgctc | ttcttcctct | gtgctatgta | cgcgcccatc | 540 |
| tgcaccattg | acttccagca | cgagcccatc | aagccctgca | agtctgtgtg | cgagcgggcc | 600 |
| cggcagggct | gtgagcccat | cctcatcaag | taccgccact | cgtggccgga | aagcctggcc | 660 |
| tgcgaggagc | tgccagtata | tgaccgcggc | gtgtgcatct | ctccggaggc | catcgtcact | 720 |
| gccgacggag | ccgatttttcc | tatggattcc | agtaatggaa | actgtagagg | agcaagcagt | 780 |
| gaacgctgca | aatgtaaacc | agtcagagct | acacagaaga | cctatttccg | aaacaattac | 840 |
| aactatgtca | ttcgggctaa | agttaaagaa | ataaagacca | agtgtcatga | tgtgactgca | 900 |
| gtagtggagg | tgaaggagat | tttaaaggct | tctctggtaa | acattccaag | ggaaactgtg | 960 |
| aacctttata | ccagctctgg | ctgcctgtgt | cctccactta | acgttaatga | ggagtatctc | 1020 |
| atcatgggct | acgaagatga | agagcgctcc | agattactgt | tggtagaagg | ttctattgct | 1080 |
| gagaaatgga | aggatcgact | tggtaaaaaa | gttaagcggt | gggatatgaa | gctccgtcat | 1140 |
| cttggactga | atacaagtga | ttctagccat | agtgattcca | ctcagagtca | gaagcctggc | 1200 |
| aggaattcta | actcccggca | agcacgcaac | taaatcctga | aatgcagaaa | atcctcagtg | 1260 |
| gacttcctat | taagacttgc | attgctggac | tagcaaaggc | aaattgcact | attgcacgtc | 1320 |
| atagtctatt | ttttagccac | aaaaatcagg | tggtaactga | tattacttct | atttttttctt | 1380 |
| ttgttttctg | cttttctcct | tccccccattc | ccttttttgt | ggtctgagta | cagatcctta | 1440 |
| aatatattat | atgtattcta | tttcactaat | catgggaaaa | ctgttctttg | caataataat | 1500 |
| aaattaaaca | tgttgatacc | agggcctctt | tgctggagta | aatgttaatt | tgctgttctg | 1560 |
| cacccagatt | gggaatgcaa | tattggatgc | aaagagagat | ttctggtata | cagagaaagc | 1620 |
| tagataggct | gtaaagcata | ctttgctgat | ctaattacag | cctcattctt | gcatgccttt | 1680 |
| tggcattctc | ctcacgctta | gaaagttcta | aatgtttata | aaggtaaaat | gacagtttga | 1740 |
| aatcaaatgc | caacaggcag | agcaatcaag | caccaggaag | catttatgaa | gaaatgacac | 1800 |
| atgagatgaa | ttatttgcaa | gattggcagg | aagcaaaata | aatagcatta | ggagctgggg | 1860 |
| atagagcatt | ttgcctgact | gagaagcaca | actgaagcta | gtagctgttg | gggtgttaac | 1920 |
| agcagcattt | ttcttttgac | gatacatttg | tttgtctgtg | aatatattga | tcagcattag | 1980 |
| agcagtggat | tgtgaccaga | catcaggtgt | tatcagcata | gctctgttta | atttgcttcc | 2040 |

-continued

```
ttttagatga acgcattggt gtctttttt tcttctttta aaataaatct cccttgctgc    2100
atttgaccag gaaaagaaag catatatgca tgtgcaccgg gctgttattt ttaagatatg    2160
tagctctata aaacgctata gtcaaaagat ggtaaaatgt gcaagattct gggtgtgtgt    2220
attaatgtgt gtgtgtccgc atacactcac actcaagctg aagtgaacga caggcctgtg    2280
cactggcctg cactttatca tttggatttg tgctgtttaa tgctcagtaa aatatgctta    2340
ataaaaggaa aaaaaaaaaa aaaaaaaaaa aaaa                                2374
```

<210> SEQ ID NO 2
<211> LENGTH: 325
<212> TYPE: PRT
<213> ORGANISM: Bos taurus

<400> SEQUENCE: 2

```
Met Val Cys Gly Ser Arg Gly Gly Met Leu Leu Leu Pro Ala Gly Leu
  1               5                  10                  15

Leu Ala Leu Ala Ala Leu Cys Leu Leu Arg Val Pro Gly Ala Arg Ala
             20                  25                  30

Ala Ala Cys Glu Pro Val Arg Ile Pro Leu Cys Lys Ser Leu Pro Trp
         35                  40                  45

Asn Met Thr Lys Met Pro Asn His Leu His His Ser Thr Gln Ala Asn
 50                  55                  60

Ala Ile Leu Ala Ile Glu Gln Phe Glu Gly Leu Leu Gly Thr His Cys
 65                  70                  75                  80

Ser Pro Asp Leu Leu Phe Phe Leu Cys Ala Met Tyr Ala Pro Ile Cys
                 85                  90                  95

Thr Ile Asp Phe Gln His Glu Pro Ile Lys Pro Cys Lys Ser Val Cys
            100                 105                 110

Glu Arg Ala Arg Gln Gly Cys Glu Pro Ile Leu Ile Lys Tyr Arg His
        115                 120                 125

Ser Trp Pro Glu Ser Leu Ala Cys Glu Glu Leu Pro Val Tyr Asp Arg
    130                 135                 140

Gly Val Cys Ile Ser Pro Glu Ala Ile Val Thr Ala Asp Gly Ala Asp
145                 150                 155                 160

Phe Pro Met Asp Ser Ser Asn Gly Asn Cys Arg Gly Ala Ser Ser Glu
                165                 170                 175

Arg Cys Lys Cys Lys Pro Val Arg Ala Thr Gln Lys Thr Tyr Phe Arg
            180                 185                 190

Asn Asn Tyr Asn Tyr Val Ile Arg Ala Lys Val Lys Glu Ile Lys Thr
        195                 200                 205

Lys Cys His Asp Val Thr Ala Val Val Glu Val Lys Glu Ile Leu Lys
    210                 215                 220

Ala Ser Leu Val Asn Ile Pro Arg Glu Thr Val Asn Leu Tyr Thr Ser
225                 230                 235                 240

Ser Gly Cys Leu Cys Pro Pro Leu Asn Val Asn Glu Glu Tyr Leu Ile
                245                 250                 255

Met Gly Tyr Glu Asp Glu Glu Arg Ser Arg Leu Leu Leu Val Glu Gly
            260                 265                 270

Ser Ile Ala Glu Lys Trp Lys Asp Arg Leu Gly Lys Lys Val Lys Arg
        275                 280                 285

Trp Asp Met Lys Leu Arg His Leu Gly Leu Asn Thr Ser Asp Ser Ser
    290                 295                 300

His Ser Asp Ser Thr Gln Ser Gln Lys Pro Gly Arg Asn Ser Asn Ser
```

```
                305                 310                 315                 320

Arg Gln Ala Arg Asn
            325

<210> SEQ ID NO 3
<211> LENGTH: 1484
<212> TYPE: DNA
<213> ORGANISM: Homo sapiens

<400> SEQUENCE: 3
cggggcctgg gcggsagggg cggtggctgg agctcggtaa agctcgtggg accccattgg      60
gggaatttga tccaaggaag cggtgattgc cggggagga gaagctccca gatccttgtg     120
tccacttgca gcggggagg cggagacgcg gagcgggcct tttggcgtcc actgcgcggc     180
tgcaccctgc cccatcctgc cgggatcatg gtctgcggca gcccgggagg gatgctgctg     240
ctgcgggccg ggctgcttgc cctggctgct ctctgcctgc tccgggtgcc cggggctcgg     300
gctgcagcct gtgagcccgt ccgcatcccc ctgtgcaagt ccctgccctg gaacatgact     360
aagatgccca accacctgca ccacagcact caggccaacg ccatcctggc catcgagcag     420
ttcgaaggtc tgctgggcac ccactgcagc cccgatctgc tcttcttcct ctgtgccatg     480
tacgcgccca tctgcaccat tgacttccag cacgagccca tcaagccctg taagtctgtg     540
tgcgagcggg cccggcaggg ctgtgagccc atactcatca agtaccgcca ctcgtggccg     600
gagaacctgg cctgcgagga gctgccagtg tacgacaggg gcgtgtgcat ctctcccgag     660
gccatcgtta ctgcggacgg agctgatttt cctatggatt ctagtaacgg aaactgtaga     720
ggggcaagca gtgaacgctg taaatgtaag cctattagag ctacacagaa gacctatttc     780
cggaacaatt acaactatgt cattcgggct aaagttaaag agataaagac taagtgccat     840
gatgtgactg cagtagtgga ggtgaaggag attctaaagt cctctctggt aaacattcca     900
cgggacactg tcaacctcta taccagctct ggctgcctct gccctccact taatgttaat     960
gaggaatata tcatcatggg ctatgaagat gaggaacgtt ccagattact cttggtggaa    1020
ggctctatag ctgagaagtg gaaggatcga ctcggtaaaa aagttaagcg ctgggatatg    1080
aagcttcgtc atcttggact cagtaaaagt gattctagca atagtgattc cactcagagt    1140
cagaagtctg gcaggaactc gaaccccgg caagcacgca actaaatccc gaaatacaaa    1200
aagtaacaca gtggacttcc tattaagact tacttgcatt gctggactag caaaggaaaa    1260
ttgcactatt gcacatcata ttctattgtt tactataaaa atcatgtgat aactgattat    1320
tacttctgtt tctcttttgg tttctgcttc tctcttctct caaccccttt gtaatggttt    1380
gggggcagac tcttaagtat attgtgagtt ttctatttca ctaatcatga gaaaaactgt    1440
tcttttgcaa taataataaa ttaaacatgc tgttaaaaaa aaaa                     1484

<210> SEQ ID NO 4
<211> LENGTH: 325
<212> TYPE: PRT
<213> ORGANISM: Homo sapiens

<400> SEQUENCE: 4

Met Val Cys Gly Ser Pro Gly Gly Met Leu Leu Leu Arg Ala Gly Leu
  1               5                  10                  15

Leu Ala Leu Ala Ala Leu Cys Leu Leu Arg Val Pro Gly Ala Arg Ala
             20                  25                  30

Ala Ala Cys Glu Pro Val Arg Ile Pro Leu Cys Lys Ser Leu Pro Trp
         35                  40                  45
```

```
Asn Met Thr Lys Met Pro Asn His Leu His Ser Thr Gln Ala Asn
    50                  55                  60

Ala Ile Leu Ala Ile Glu Gln Phe Glu Gly Leu Leu Gly Thr His Cys
65                  70                  75                  80

Ser Pro Asp Leu Leu Phe Phe Leu Cys Ala Met Tyr Ala Pro Ile Cys
                85                  90                  95

Thr Ile Asp Phe Gln His Glu Pro Ile Lys Pro Cys Lys Ser Val Cys
            100                 105                 110

Glu Arg Ala Arg Gln Gly Cys Glu Pro Ile Leu Ile Lys Tyr Arg His
            115                 120                 125

Ser Trp Pro Glu Asn Leu Ala Cys Glu Glu Leu Pro Val Tyr Asp Arg
    130                 135                 140

Gly Val Cys Ile Ser Pro Glu Ala Ile Val Thr Ala Asp Gly Ala Asp
145                 150                 155                 160

Phe Pro Met Asp Ser Ser Asn Gly Asn Cys Arg Gly Ala Ser Ser Glu
                165                 170                 175

Arg Cys Lys Cys Lys Pro Ile Arg Ala Thr Gln Lys Thr Tyr Phe Arg
            180                 185                 190

Asn Asn Tyr Asn Tyr Val Ile Arg Ala Lys Val Lys Glu Ile Lys Thr
            195                 200                 205

Lys Cys His Asp Val Thr Ala Val Val Glu Val Lys Glu Ile Leu Lys
    210                 215                 220

Ser Ser Leu Val Asn Ile Pro Arg Asp Thr Val Asn Leu Tyr Thr Ser
225                 230                 235                 240

Ser Gly Cys Leu Cys Pro Pro Leu Asn Val Asn Glu Glu Tyr Ile Ile
                245                 250                 255

Met Gly Tyr Glu Asp Glu Arg Ser Arg Leu Leu Leu Val Glu Gly
            260                 265                 270

Ser Ile Ala Glu Lys Trp Lys Asp Arg Leu Gly Lys Lys Val Lys Arg
    275                 280                 285

Trp Asp Met Lys Leu Arg His Leu Gly Leu Ser Lys Ser Asp Ser Ser
    290                 295                 300

Asn Ser Asp Ser Thr Gln Ser Gln Lys Ser Gly Arg Asn Ser Asn Pro
305                 310                 315                 320

Arg Gln Ala Arg Asn
                325

<210> SEQ ID NO 5
<211> LENGTH: 111
<212> TYPE: PRT
<213> ORGANISM: Rattus norvegicus

<400> SEQUENCE: 5

Cys Gln Pro Ile Ser Ile Pro Leu Cys Thr Asp Ile Ala Tyr Asn Gln
1               5                   10                  15

Thr Ile Met Pro Asn Leu Leu Gly His Thr Asn Gln Glu Asp Ala Gly
            20                  25                  30

Leu Glu Val His Gln Phe Tyr Pro Leu Val Lys Val Gln Cys Ser Ala
            35                  40                  45

Glu Leu Lys Phe Phe Leu Cys Ser Met Tyr Ala Pro Val Cys Thr Val
        50                  55                  60

Leu Glu Gln Ala Leu Pro Pro Cys Arg Ser Leu Cys Glu Arg Ala Gln
65                  70                  75                  80

Gly Cys Glu Ala Leu Met Asn Lys Phe Gly Phe Gln Trp Pro Asp Thr
```

```
                      85                  90                  95
Leu Lys Cys Glu Lys Phe Pro Val His Gly Arg Gly Glu Leu Cys
            100                 105                 110

<210> SEQ ID NO 6
<211> LENGTH: 111
<212> TYPE: PRT
<213> ORGANISM: Drosophila melanogaster

<400> SEQUENCE: 6

Cys Glu Pro Ile Thr Ile Ser Ile Cys Lys Asn Ile Pro Tyr Asn Met
1               5                   10                  15

Thr Ile Met Pro Asn Leu Ile Gly His Thr Lys Gln Glu Glu Ala Gly
            20                  25                  30

Leu Glu Val His Gln Phe Ala Pro Leu Val Lys Ile Gly Cys Ser Asp
        35                  40                  45

Asp Leu Gln Leu Phe Leu Cys Ser Leu Tyr Val Pro Val Cys Thr Ile
    50                  55                  60

Leu Glu Arg Pro Ile Pro Pro Cys Arg Ser Leu Cys Glu Ser Ala Arg
65                  70                  75                  80

Val Cys Glu Lys Leu Met Lys Thr Tyr Asn Phe Asn Trp Pro Glu Asn
                85                  90                  95

Leu Glu Cys Ser Lys Phe Pro Val His Gly Gly Glu Asp Leu Cys
            100                 105                 110

<210> SEQ ID NO 7
<211> LENGTH: 319
<212> TYPE: PRT
<213> ORGANISM: Xenopus laevis

<400> SEQUENCE: 7

Met Ser Pro Thr Arg Lys Leu Asp Ser Phe Leu Leu Leu Val Ile Pro
1               5                   10                  15

Gly Leu Val Leu Leu Leu Pro Asn Ala Tyr Cys Ala Ser Cys Glu
            20                  25                  30

Pro Val Arg Ile Pro Met Cys Lys Ser Met Pro Trp Asn Met Thr Lys
        35                  40                  45

Met Pro Asn His Leu His His Ser Thr Gln Ala Asn Ala Ile Leu Ala
    50                  55                  60

Ile Glu Gln Phe Glu Gly Leu Leu Thr Thr Glu Cys Ser Gln Asp Leu
65                  70                  75                  80

Leu Phe Phe Leu Cys Ala Met Tyr Ala Pro Ile Cys Thr Ile Asp Phe
                85                  90                  95

Gln His Glu Pro Ile Lys Pro Cys Lys Ser Val Cys Glu Arg Ala Arg
            100                 105                 110

Ala Gly Cys Glu Pro Ile Leu Ile Lys Tyr Arg His Thr Trp Pro Glu
        115                 120                 125

Ser Leu Ala Cys Glu Glu Leu Pro Val Tyr Asp Arg Gly Val Cys Ile
    130                 135                 140

Ser Pro Glu Ala Ile Val Thr Val Glu Gln Gly Thr Asp Ser Met Pro
145                 150                 155                 160

Asp Phe Pro Met Asp Ser Asn Asn Gly Asn Cys Gly Ser Thr Ala Gly
                165                 170                 175

Glu His Cys Lys Cys Lys Pro Met Lys Ala Ser Gln Lys Thr Tyr Leu
            180                 185                 190

Lys Asn Asn Tyr Asn Tyr Val Ile Arg Ala Lys Val Lys Glu Val Lys
```

```
                    195                 200                 205
Val Lys Cys His Asp Ala Thr Ala Ile Val Glu Val Lys Glu Ile Leu
            210                 215                 220
Lys Ser Ser Leu Val Asn Ile Pro Lys Asp Thr Val Thr Leu Tyr Thr
225                 230                 235                 240
Asn Ser Gly Cys Leu Cys Pro Gln Leu Val Ala Asn Glu Glu Tyr Ile
                245                 250                 255
Ile Met Gly Tyr Glu Asp Lys Glu Arg Thr Arg Leu Leu Val Glu
            260                 265                 270
Gly Ser Leu Ala Glu Lys Trp Arg Asp Arg Leu Ala Lys Lys Val Lys
            275                 280                 285
Arg Trp Asp Gln Lys Leu Arg Arg Pro Arg Lys Ser Lys Asp Pro Val
        290                 295                 300
Ala Pro Ile Pro Asn Lys Asn Ser Asn Ser Arg Gln Ala Arg Ser
305                 310                 315

<210> SEQ ID NO 8
<211> LENGTH: 319
<212> TYPE: PRT
<213> ORGANISM: Artificial Sequence
<220> FEATURE:
<223> OTHER INFORMATION: Consensus sequence

<400> SEQUENCE: 8

Met Val Cys Gly Ser Gly Gly Met Leu Leu Leu Ala Gly Leu Leu Ala
1               5                   10                  15
Leu Ala Ala Leu Cys Leu Leu Arg Val Pro Gly Ala Arg Ala Ala Ala
                20                  25                  30
Cys Glu Pro Val Arg Ile Pro Leu Cys Lys Ser Leu Pro Trp Asn Met
            35                  40                  45
Thr Lys Met Pro Asn His Leu His His Ser Thr Gln Ala Asn Ala Ile
        50                  55                  60
Leu Ala Ile Glu Gln Phe Glu Gly Leu Leu Gly Thr His Cys Ser Pro
65                  70                  75                  80
Asp Leu Leu Phe Phe Leu Cys Ala Met Tyr Ala Pro Ile Cys Thr Ile
                85                  90                  95
Asp Phe Gln His Glu Pro Ile Lys Pro Cys Lys Ser Val Cys Glu Arg
            100                 105                 110
Ala Arg Gln Gly Cys Glu Pro Ile Leu Ile Lys Tyr Arg His Ser Trp
        115                 120                 125
Pro Glu Ser Leu Ala Cys Glu Glu Leu Pro Val Tyr Asp Arg Gly Val
130                 135                 140
Cys Ile Ser Pro Glu Ala Ile Val Thr Ala Asp Gly Ala Asp Phe Pro
145                 150                 155                 160
Met Asp Ser Ser Asn Gly Asn Cys Arg Gly Ala Ser Ser Glu Arg Cys
                165                 170                 175
Lys Cys Lys Pro Arg Ala Thr Gln Lys Thr Tyr Phe Arg Asn Asn Tyr
            180                 185                 190
Asn Tyr Val Ile Arg Ala Lys Val Lys Glu Ile Lys Thr Lys Cys His
        195                 200                 205
Asp Val Thr Ala Val Val Glu Val Lys Glu Ile Leu Lys Ser Ser Leu
    210                 215                 220
Val Asn Ile Pro Arg Asp Thr Val Asn Leu Tyr Thr Ser Ser Gly Cys
225                 230                 235                 240
Leu Cys Pro Pro Leu Asn Val Asn Glu Glu Tyr Ile Ile Met Gly Tyr
```

-continued

```
                    245                 250                 255
Glu Asp Glu Glu Arg Ser Arg Leu Leu Leu Val Glu Gly Ser Ile Ala
            260                 265                 270

Glu Lys Trp Lys Asp Arg Leu Gly Lys Lys Val Lys Arg Trp Asp Met
        275                 280                 285

Lys Leu Arg His Leu Gly Leu Ser Asp Ser Ser Asp Ser Thr Gln
        290                 295                 300

Ser Gln Lys Pro Gly Arg Asn Ser Asn Ser Arg Gln Ala Arg Asn
305                 310                 315

<210> SEQ ID NO 9
<211> LENGTH: 30
<212> TYPE: PRT
<213> ORGANISM: Artificial Sequence
<220> FEATURE:
<223> OTHER INFORMATION: Synthetic peptide

<400> SEQUENCE: 9

Glu Thr Val Asn Leu Tyr Thr Ser Ala Gly Cys Leu Cys Pro Pro Leu
1               5                   10                  15

Asn Val Asn Glu Glu Tyr Leu Ile Met Gly Tyr Glu Phe Pro
            20                  25                  30

<210> SEQ ID NO 10
<211> LENGTH: 21
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (1)...(21)
<223> OTHER INFORMATION: n = A,T,C or G

<400> SEQUENCE: 10
garachgtsa ayctbtayac n                                        21

<210> SEQ ID NO 11
<211> LENGTH: 18
<212> TYPE: DNA
<213> ORGANISM: Artificial Sequence
<220> FEATURE:
<223> OTHER INFORMATION: oligonucleotide primer
<220> FEATURE:
<221> NAME/KEY: misc_feature
<222> LOCATION: (1)...(18)
<223> OTHER INFORMATION: n = A,T,C or G

<400> SEQUENCE: 11
raaytcrtan cccatnat                                            18

<210> SEQ ID NO 12
<211> LENGTH: 19
<212> TYPE: PRT
<213> ORGANISM: Artificial Sequence
<220> FEATURE:
<223> OTHER INFORMATION: tryptic fragment
<220> FEATURE:
<221> NAME/KEY: VARIANT
<222> LOCATION: (1)...(19)
<223> OTHER INFORMATION: Xaa = Asp or His

<400> SEQUENCE: 12

Gly Val Cys Ile Ser Pro Glu Ala Ile Val Thr Ala Xaa Gly Ala Asp
1               5                   10                  15
```

Phe Pro Met

<210> SEQ ID NO 13
<211> LENGTH: 9
<212> TYPE: PRT
<213> ORGANISM: Artificial Sequence
<220> FEATURE:
<223> OTHER INFORMATION: tryptic fragment

<400> SEQUENCE: 13

Gln Gly Cys Glu Pro Ile Leu Ile Lys
 1               5

<210> SEQ ID NO 14
<211> LENGTH: 15
<212> TYPE: PRT
<213> ORGANISM: Artificial Sequence
<220> FEATURE:
<223> OTHER INFORMATION: tryptic fragment

<400> SEQUENCE: 14

Gln Gly Cys Glu Pro Ile Leu Ile Cys Ala Trp Pro Pro Leu Tyr
 1               5                  10                  15

<210> SEQ ID NO 15
<211> LENGTH: 28
<212> TYPE: PRT
<213> ORGANISM: Artificial Sequence
<220> FEATURE:
<223> OTHER INFORMATION: tryptic fragment

<400> SEQUENCE: 15

Glu Thr Val Asn Leu Tyr Thr Ser Ala Gly Cys Leu Cys Pro Leu
 1               5                  10                  15

Asn Val Asn Glu Glu Tyr Leu Ile Met Gly Tyr Glu
            20                  25

<210> SEQ ID NO 16
<211> LENGTH: 28
<212> TYPE: PRT
<213> ORGANISM: Artificial Sequence
<220> FEATURE:
<223> OTHER INFORMATION: synthetic peptide

<400> SEQUENCE: 16

Glu Thr Val Asn Leu Tyr Thr Ser Ser Gly Cys Leu Cys Pro Leu
 1               5                  10                  15

Asn Val Asn Glu Glu Tyr Leu Ile Met Gly Tyr Glu
            20                  25

<210> SEQ ID NO 17
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 17
gctctggctg cctgtgtcct ccacttaacg                                    30

<210> SEQ ID NO 18
<211> LENGTH: 30
<212> TYPE: DNA
<213> ORGANISM: Artificial Sequence
<220> FEATURE:
<223> OTHER INFORMATION: oligonucleotide primer

```
<400> SEQUENCE: 18
cctccactta acgttaatga ggagtatctc                                    30

<210> SEQ ID NO 19
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 19
tggaacatga ctaagatgcc c                                             21

<210> SEQ ID NO 20
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 20
catatactgg cagctcctcg                                               20

<210> SEQ ID NO 21
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 21
gtcttttggg aagccttcat gg                                            22

<210> SEQ ID NO 22
<211> LENGTH: 22
<212> TYPE: DNA
<213> ORGANISM: Artificial Sequence
<220> FEATURE:
<223> OTHER INFORMATION: oligonucleotide primer

<400> SEQUENCE: 22
gcatcgtggc atttcacttt ca                                            22

<210> SEQ ID NO 23
<211> LENGTH: 1291
<212> TYPE: DNA
<213> ORGANISM: Xenopus laevis

<400> SEQUENCE: 23
tttactgtgc cagtcttccc tgtaaccagc gacctgtatt cccccaagta agcctacaca    60
tacaggttgg gcagaataac aatgtctcca acaaggaaat tggactcatt cctgctactg   120
gtcatacctg gactggtgct tctcttatta cccaatgctt actgtgcttc gtgtgagcct   180
gtgcggattc ccatgtgcaa atctatgcca tggaacatga ccaagatgcc caaccatctc   240
caccacagca ctcaagccaa tgctatcctg gcaattgaac agtttgaagg tttgctgacc   300
actgaatgta gccaggacct tttgttcttt ctgtgtgcca tgtatgcccc catttgtacc   360
atcgatttcc agcatgaacc aattaagcct tgcaagtccg tgtgcgaaag gccagggcc   420 ggctgtgagc ccattctcat aaagtaccgg cacacttggc cagagagcct ggcatgtgaa   480
gagctgcccg tatatgacag aggagtctgc atctccccag aggctatcgt cacagtggaa   540
```

```
caaggaacag attcaatgcc agacttcccc atggattcaa acaatggaaa ttgcggaagc      600
acggcaggtg agcactgtaa atgcaagccc atgaaggctt cccaaaagac gtatctcaag      660
aataattaca attatgtaat cagagcaaaa gtgaaagagg tgaaagtgaa atgccacgac      720
gcaacagcaa ttgtggaagt aaaggagatt ctcaagtctt ccctagtgaa cattcctaaa      780
gacacagtga cactgtacac caactcaggc tgcttgtgcc cccagcttgt tgccaatgag      840
gaatacataa ttatgggcta tgaagacaaa gagcgtacca ggcttctact agtggaagga      900
tccttggccg aaaaatggag agatcgtctt gctaagaaag tcaagcgctg ggatcaaaag      960
cttcgacgtc ccaggaaaag caaagacccc gtggctccaa ttcccaacaa aaacagcaat     1020
tccagacaag cgcgtagtta gactaacgga aaggtgtatg gaaactctat ggactttgaa     1080
actaagattt gcattgttgg aagagcaaaa aagaaattgc actacagcac gttatattct     1140
attgtttact acaagaagct ggtttagttg attgtagttc tcctttcctt ctttttttta     1200
taactatatt gcacgtgttc caggcagttt atcaacttcc agtgacagag cagtgactga     1260
atgtagctaa gagcctatca tctgatcact a                                     1291
```